US012324697B2

(12) United States Patent
Miyake et al.

(10) Patent No.: US 12,324,697 B2
(45) Date of Patent: Jun. 10, 2025

(54) RADIATION IMAGING SYSTEM, IMAGING CONTROL APPARATUS, AND RADIATION IMAGING METHOD

(71) Applicant: Konica Minolta, Inc., Tokyo (JP)

(72) Inventors: Nobuyuki Miyake, Yokohama (JP); Tatsuya Takagi, Mitaka (JP); Kentaro Hara, Hino (JP); Ichirou Hamamoto, Fuchu (JP)

(73) Assignee: KONICA MINOLTA, INC., Tokyo (JP)

( * ) Notice: Subject to any disclaimer, the term of this patent is extended or adjusted under 35 U.S.C. 154(b) by 143 days.

(21) Appl. No.: 17/501,543

(22) Filed: Oct. 14, 2021

(65) Prior Publication Data

US 2022/0117574 A1 Apr. 21, 2022

(30) Foreign Application Priority Data

Oct. 19, 2020 (JP) ................................ 2020-175059

(51) Int. Cl.
*A61B 6/00* (2024.01)

(52) U.S. Cl.
CPC .............. *A61B 6/542* (2013.01); *A61B 6/488* (2013.01); *A61B 6/5205* (2013.01); *A61B 6/545* (2013.01)

(58) Field of Classification Search
CPC ......... A61B 6/488; A61B 6/542; A61B 6/545; A61B 6/5205
See application file for complete search history.

(56) References Cited

U.S. PATENT DOCUMENTS

| 6,782,071 B1* | 8/2004 | Tsuyuki ................ A61B 6/032 378/20 |
| 2008/0037714 A1* | 2/2008 | Sakaida ................ A61B 6/032 378/207 |

(Continued)

FOREIGN PATENT DOCUMENTS

| JP | 2019-126709 A | 8/2019 |
| WO | 2013/015266 A1 | 1/2013 |

(Continued)

OTHER PUBLICATIONS

Office Action, dated May 7, 2025, which was issued for the corresponding Japanese Patent Application No. 2024-125537, 8 pages, with English translation.

*Primary Examiner* — Keith M Raymond
*Assistant Examiner* — Milton Truong
(74) *Attorney, Agent, or Firm* — LUCAS & MERCANTI, LLP

(57) ABSTRACT

A radiation imaging system includes a first hardware processor. The first hardware processor executes control such that before main imaging is executed at a main dose, pre-imaging is executed at a pre-dose that is lower than the main dose. The first hardware processor derives an imaging condition for the main imaging based on a pre-image acquired in the pre-imaging, switches a control mode to one of a pre-image checking mode and a short-time imaging mode, and notifies which control mode between the pre-image checking mode and the short-time imaging mode is used to execute the control. The pre-image checking mode being a mode in which the pre-image is displayed after executing the pre-imaging. The short-time imaging mode being a mode in which the pre-image is not displayed after executing the pre-imaging before the main imaging.

15 Claims, 10 Drawing Sheets

(56) References Cited

U.S. PATENT DOCUMENTS

| 2013/0148782 | A1* | 6/2013 | Tajima | A61B 6/545 |
| | | | | 378/62 |
| 2018/0103924 | A1* | 4/2018 | Nakayama | A61B 6/585 |
| 2019/0090837 | A1* | 3/2019 | Kawamura | A61B 6/488 |
| 2019/0223822 | A1* | 7/2019 | Takagi | A61B 6/544 |

FOREIGN PATENT DOCUMENTS

| WO | 2014/108929 A1 | 7/2014 |
| WO | 2016/208229 A1 | 12/2016 |

* cited by examiner

FIG.7
| IMAGING TECHNIQUE | | DEFAULT CONTROL MODE |
|---|---|---|
| CHEST | FRONT VIEW | SHORT-TIME IMAGING MODE |
| | SIDE VIEW | SHORT-TIME IMAGING MODE |
| KNEE JOINT | FRONT VIEW | SHORT-TIME IMAGING MODE |
| | SIDE VIEW | PRE-IMAGE CHECKING MODE |
FIG.8A
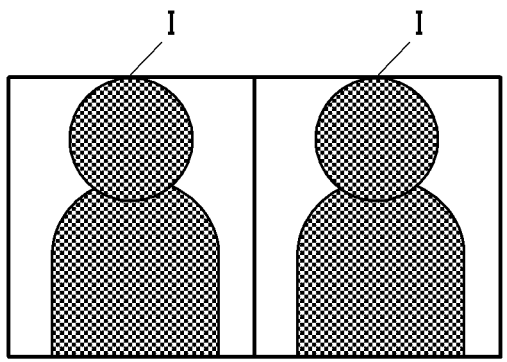
FIG.8B
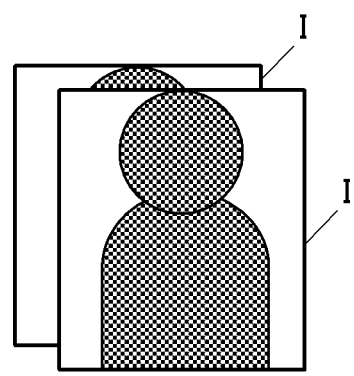
FIG.8C
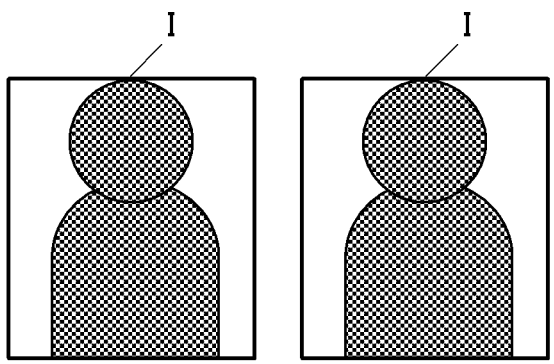
FIG.8D
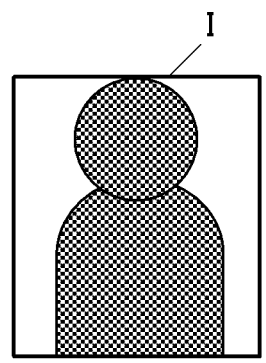

| IMAGING TECHNIQUE | | IMAGE RETAKEN RATE OF SUBJECT A | IMAGE RETAKEN RATE OF SUBJECT B |
|---|---|---|---|
| CHEST | FRONT VIEW | 3% | 4% |
| | SIDE VIEW | 4% | 4% |
| KNEE JOINT | FRONT VIEW | 5% | 5% |
| | SIDE VIEW | 20% | 6% |

| IMAGING TECHNIQUE | | IMAGE RETAKING RATE BY RADIOGRAPHER A | IMAGE RETAKING RATE BY RADIOGRAPHER B |
|---|---|---|---|
| CHEST | FRONT VIEW | 5% | 4% |
| | SIDE VIEW | 7% | 4% |
| KNEE JOINT | FRONT VIEW | 7% | 5% |
| | SIDE VIEW | 20% | 6% |

RADIATION IMAGING SYSTEM, IMAGING CONTROL APPARATUS, AND RADIATION IMAGING METHOD

CROSS-REFERENCE TO RELATED APPLICATIONS

The entire disclosure of Japanese Patent Application No 2020-175039 filed on Oct. 19, 2020 is incorporated herein by reference in its entirety.

BACKGROUND

Technological Field

The present invention relates to a radiation imaging system, an imaging control apparatus, and a radiation imaging method.

Description of the Related Art

In recent years, various technologies have been proposed regarding a radiation imaging system that executes two-step radiation imaging in winch an appropriate radiation dose for main imaging is derived based on a radiation image (pre-image) acquired in pre-imaging prior to the main imaging, and the main imaging is executed at the derived radiation dose.

For example, JP 2019-126709A describes a technology for automatically judging whether or not pre-imaging has been appropriately executed by image analysis on the pre-image, a technology for displaying the pre-image to allow a user to judge whether or not pre-imaging has been appropriately executed, a technology for setting in advance whether or not to display the pre-image, a technology for displaying the pre-image when it has been automatically judged that pre-imaging has not been appropriately executed, and the like.

In radiation imaging, the possibility of an imaging failure (main imaging executed with inappropriate positioning) differs depending on imaging attributes (imaging site, characteristics of the subject, and the like).

When executing imaging of such an imaging attribute with relatively high possibility of imaging failure, the user warns to check the pre-image and judge whether the positioning is appropriate or not by himself, even though it may take some time.

On the other hand, when executing imaging of an imaging attribute with little possibility of imaging failure, the user has a low need to determine whether or not the positioning is appropriate. Therefore, the user wants to shorten the time between the end of pre-imaging and the start of the main imaging as much as possible so as to execute the main imaging before the subject moves his or her body a lot.

However, it is not possible according to the technology described in JP 2019-126709A to property execute both of the two different imaging attributes described above.

In addition, according to the technology described in JP 2019-126709A, the user cannot see whether or not the system is set to display the pre-image alter the pre-imaging.

Therefore, for example, although the pre-image is set to be displayed, the user may think that the pre-image is not set to be displayed, mistakenly believe that the displayed pre-image is a main image, and complete radiation imaging without executing the main imaging. In such a case, it is necessary to execute the pre-imaging and the main imaging again, and the subject is irradiated with unnecessary radiation for the amount of pre-imaging.

SUMMARY

The present invention has been made in consideration of the problems described above, and aims to enable a single device to be used for both of the two kinds of imaging with different possibilities of failure due to different imaging attributes and to enable the user to be sure of knowing whether or not the pre-image is to be displayed after pre-imaging when executing two-step radiation imaging including pre-imaging and main imaging.

In order to solve tire above problems, according to one aspect of the present invention, there is provided a radiation imaging system including a first hardware processor that executes control such that, before main imaging is executed at a main dose, pre-imaging is executed at a pre-dose that is lower than the main dose, the first hardware processor deriving an imaging condition for the main imaging based on a pre-image acquired in the pre-imaging, switching a control mode to one of a pre-image checking mode and a short-time imaging mode, and notifying which control mode between the pre-image checking mode and the short-time imaging mode is used to execute the control, the pre-image checking mode being a mode in which the pre-image is displayed after executing the pre-imaging, and the short-time imaging mode being a mode in which the pre-image is not displayed after executing the pre-imaging before the main imaging.

Also, according to another aspect of the present invention, there is provided an imaging control apparatus that is a part of a radiation imaging system including a first hardware processor that executes control such that, before main imaging is executed at a main dose, pre-imaging is executed at a pre-dose that is lower than the main dose, the first hardware processor deriving an imaging condition for the main imaging based on a pre-image acquired in the pre-imaging, switching a control mode to one of a pre-image checking mode and a short-time imaging mode, and outputting which control mode between the pre-image checking mode and the short-time imaging mode is used to execute the control, the pre-image checking mode being a mode in which the pre-image is displayed after executing the pre-imaging, and the short-time imaging mode being a mode in which the pre-image is not displayed after executing the pre-imaging before the main imaging.

Also, according to another aspect of the present invention, there is provided a radiation imaging method using a radiation imaging system including a first hardware processor that executes control such that, before main imaging is executed at a main dose, pre-imaging is executed at a pre-dose that is lower than the main dose and deriving an imaging condition for the main imaging based on a pre-image acquired in the pre-imaging, the method comprising:

switching a control mode of the first hardware processor to one of a pre-image checking mode and a short-time imaging mode, the pre-image checking mode being a mode in which the pre-image is displayed after executing the pre-imaging, and the short-time imaging mode being a mode in which the pre-image is not displayed after executing the pre-imaging before the main imaging; and notifying the radiation imaging system which control mode between the pre-image checking mode and the short-time imaging mode the first hardware processor is using to execute the control.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 7 is a table showing an example of a mode decision table stored by the imaging control apparatus of FIG. 5;

FIG. 8A is a diagram showing icons displayed by the imaging control apparatus of FIG. 5;

FIG. 8B is a diagram showing icons displayed by the imaging control apparatus of FIG. 5;

FIG. 8C is a diagram showing icons displayed by the imaging control apparatus of FIG. 5:

FIG. 8D is a diagram showing icons displayed by the imaging control apparatus of FIG. 5;

DETAILED DESCRIPTION OF THE EMBODIMENTS

Hereinafter, one or more embodiments of the present invention will be described with reference to the drawings. However, the scope of the present invention is not limited to the disclosed embodiments.

1. Radiation Imaging System

First of all, a schematic configuration of a radiation imaging system (hereinafter, system 100) according to the present embodiment is described.

Figure 1:
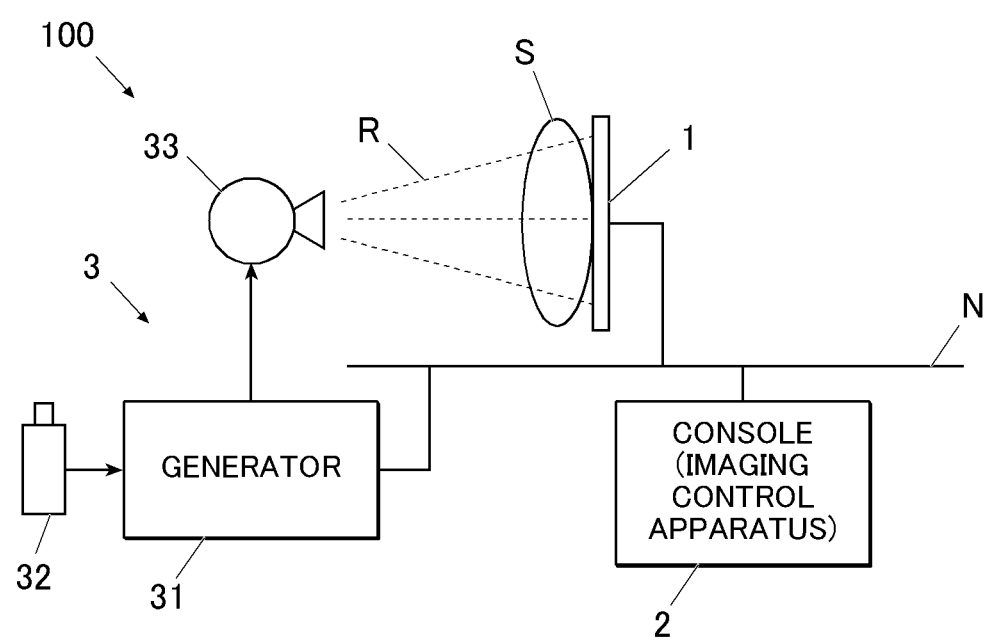
FIG. 1 is a block diagram of an example of a radiation imaging system according to the present invention.
Figure 2A:
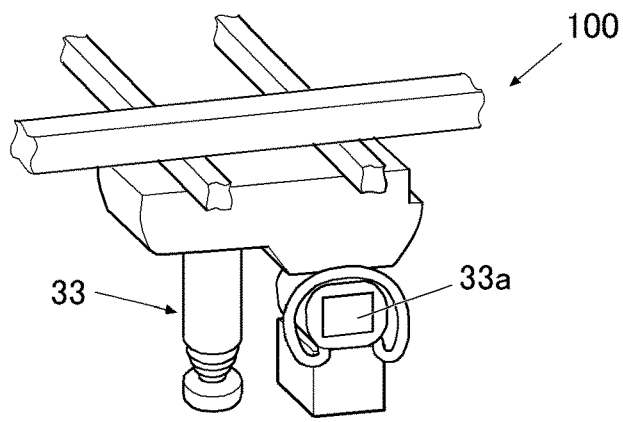
FIG. 2A is a perspective view of the radiation imaging system of FIG. 1.
Figure 2A:
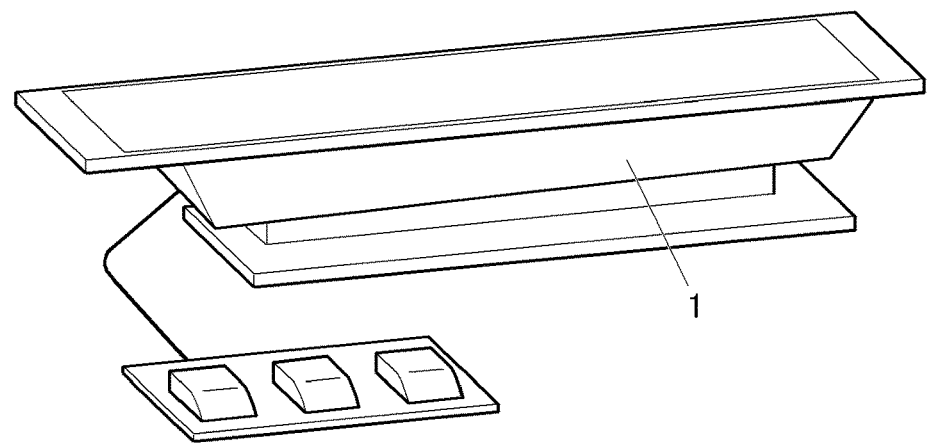
Figure 2B:
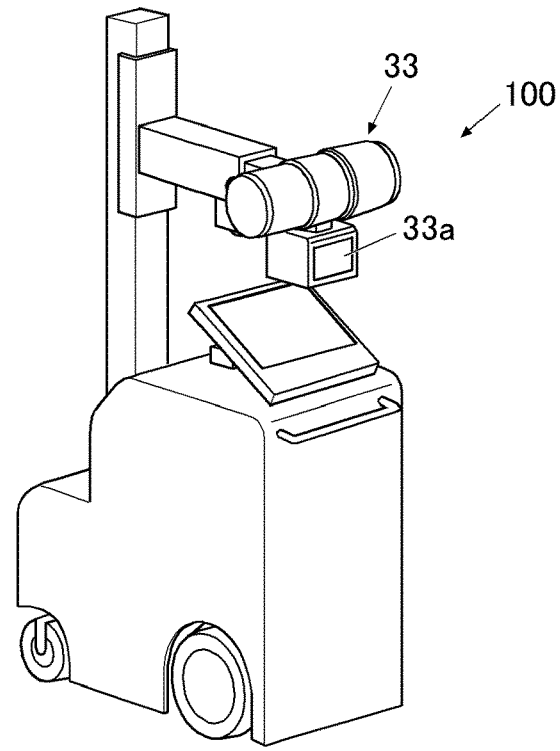
FIG. 2B is a perspective view of the radiation imaging system of FIG. 1.

FIG. 1 is a block diagram showing the system 100, and FIG. 2A and FIG. 2B are perspective view showing the system 100.

As shown in FIG. 1, the system 100 includes, for example, a radiation detector (hereinafter, detector 1) and a console 2.

The system 100 according to the present embodiment further includes a radiation generating apparatus (hereinafter, generating apparatus 3) and image managing apparatus 4.

The apparatuses 1 to 3 are able to communicate with each other through a communication network N (LAN (Local Area Network), WAN (Wide Area Network), internet, and the like), for example.

The system 100 may be able to communicate with a Hospital Information System (HIS), a Radiology Information System (RIS), a Picture Archiving and Communication System (PACS), a dynamic analyzing apparatus, or the like (not shown in the drawings).

The system 100 may be fixed in an imaging room as shown in FIG. 2A, for example, or may be configured to be a movable examination car as shown in FIG. 2B.

[1-1. Radiation Generating Apparatus]

The generating apparatus 3 includes, as shown in FIG. 1, a generator 31, an irradiating instruction switch 32, and a tubular bulb 33.

[1-1-1. Irradiating Instruction Switch]

The irradiating instruction switch 32 has two-step buttons.

When only the first step button is pressed, the irradiating instruction switch 32 outputs a signal indicating that to the generator 31.

When both the first and second buttons are pressed, the irradiating instruction switch 32 outputs a signal indicating that to the generator 31.

[1-1-2. Generator]

Based on the signal that only the first step button of the irradiating instruction switch 32 is pressed, the generator 31 transmits an instruction signal to the tubular bulb 33 to start preparation for emitting radiation R.

Based on the signal indicating pressing of the first and/or the second button(s) of the irradiating instruction switch 32, the generator 31 applies voltage and current to the tubular bulb 33 according to preset imaging condition(s) (for example, conditions regarding the imaging target (either a person or an object, hereinafter referred to as "subject S"), such as the imaging site, imaging orientation, body size, and the like, and conditions regarding emission of radiation R, such as tube voltage, tube current, irradiation time, and tube current-time product (mAs value).

The details of this generator 31 will be described later

[1-1-3. Tubular Bulb]

The tubular bulb 33 starts preparations to generate radiation R in response to receiving a signal from the generator 31 indicating the start of preparations (for example, rotation of an anode rotor or applying a filament current to heat a cathode filament).

When the tube voltage and the tube current are applied from the generator 31, the tubular bulb 33 generates radiation R (for example, X-rays) at a dose depending on the applied tube voltage and the tube current for a preset irradiation time.

In addition, the tubular bulb 33 can move in an X-axis direction, a Y-axis direction orthogonal to the X-axis, and a Z-axis direction orthogonal to the X-axis and the Y-axis, and change the direction of an irradiation port of the radiation R by notating around the rotation axis in parallel with the X-axis, Y-axis, and Z-axis.

In addition, the tubular bulb 33 according to this embodiment has a tubular bulb display 33a as shown in FIG. 2A.

The tubular bulb display 33a displays a screen according to the image signal received from a second controller 311 (second hardware processor) described later of the generator 31 or a controller 21 (first hardware processor) described later of the console 2.

The tubular bulb display 33a may be a housing integrated with the tubular bulb 33, or may be a housing separated from and attached to the tubular bulb 33.

The tubular bulb display 33a of the present embodiment is configured to change at least one of its position and orientation following a change in at least one of the position and orientation of the tubular bulb 33. This allows the user to look at the display of the tubular bulb display 33a while adjusting at least one of the position and orientation of the tubular bulb 33.

[1-1-4 Outline of Operation of Radiation Generating Apparatus]

The generating apparatus 3 configured in this way generates radiation R in a manner according to the form of the radiation image to be generated (still image, dynamic image consisting of multiple frames, or the like).

When the radiation image is a still image, radiation R is emitted only once for each pressing of the irradiating instruction switch 32.

When the radiation image is a dynamic image, for each pressing of the irradiating instruction switch 32, radiation R is emitted repeatedly in the form of pulses for a predetermined period of lime (for example, 15 times per second) or continuously for a predetermined period of time.

[1-2. Radiation Detector]

The detector 1 includes, though not shown in the drawings, a scintillator that emits light with an intensity corresponding to a dose by receiving the radiation R, a sensor board in which pixels having semiconductor elements that generate electric charges according to an intensity of received light or switch elements that store and discharge electric charges are arranged in a two-dimensional shape (matrix shape), a scanning circuit that switches on/off of each switch element, a readout circuit that reads out an amount of electric charges emitted from each pixel as a signal value, a controller that generates a radiation image from a plurality of the signal values read out by the readout circuit, and a communication unit that transmits data of the generated radiation image and various signals to the outside and receives various information and various signals.

The detector 1 stores and releases electric charges and reads out the signal value in synchronization with the timing when the radiation R is emitted from the generating apparatus 3, so that the radiation image according to the dose distribution of the emitted radiation R is generated.

When a still image is generated, the radiation image is generated only once for each pressing of the irradiating instruction switch 32.

When a dynamic image is generated, the generation of frames constituting the dynamic image is repeated a plurality of times per predetermined time (for example, 15 times per second) for each pressing of the irradiating instruction switch 32.

The detector 1 may not include a scintillator and but may directly generate electric charges when the semiconductor element receives radiation R.

In addition, the detector 1 may save and transfer the generated dynamic image in the form of image data, or may display the generated dynamic image on a display connected to the detector 1 itself in real time (for example, see through)

[1-3. Console]

The console 2 is configured with a PC, a mobile terminal, or a dedicated device.

The console 2 can set imaging conditions in the detector 1 and the generating apparatus 3 based on imaging order from an external device (RIS or the like) or an operation by a user.

The console 2 according to the present embodiment also serves as an imaging control apparatus constituting a part of the system 100.

In other words, the console 2 controls the detector 1 and the generating apparatus 3 by executing an imaging control process.

Details of the console 2 including the imaging control process w ill be described later.

[1-4. Outline of Operation of Radiographic Imaging System]

The system 100 configured as described above operates as follows.

First, the console 2 executes a control to execute the pre-imaging before the main imaging.

Specifically, the console 2 causes the generating apparatus 3 to emit a pre-dose of radiation R, which is less than a main dose in the main imaging, to the subject S located between the tubular bulb 33 of the generating apparatus 3 and the detector 1, which are placed opposite to each other with a space between them.

The detector 1 receives radiation R through the subject S, generates a pre-image of the subject S, and transmits data of the image (hereinafter referred to as "pre-image data") to the console 2.

Thereafter, the console 2 executes control for the main imaging.

Specifically, the console 2 causes the generating apparatus 3 to emit a main dose of radiation R to the subject S.

The detector 1 that has received radiation R through the subject S generates a main image of the subject S. and transmits data of the image (hereinafter referred to as "main image data") to the console 2.

The console 2 that has received the main image data generates a final radiation image (hereinafter referred to as a "final image").

[1-5. Others]

The system 100 in which the console 2 also serves as the imaging control apparatus has been described so far, but a device other titan the console 2 may also serve as the imaging control apparatus.

Figure 3:
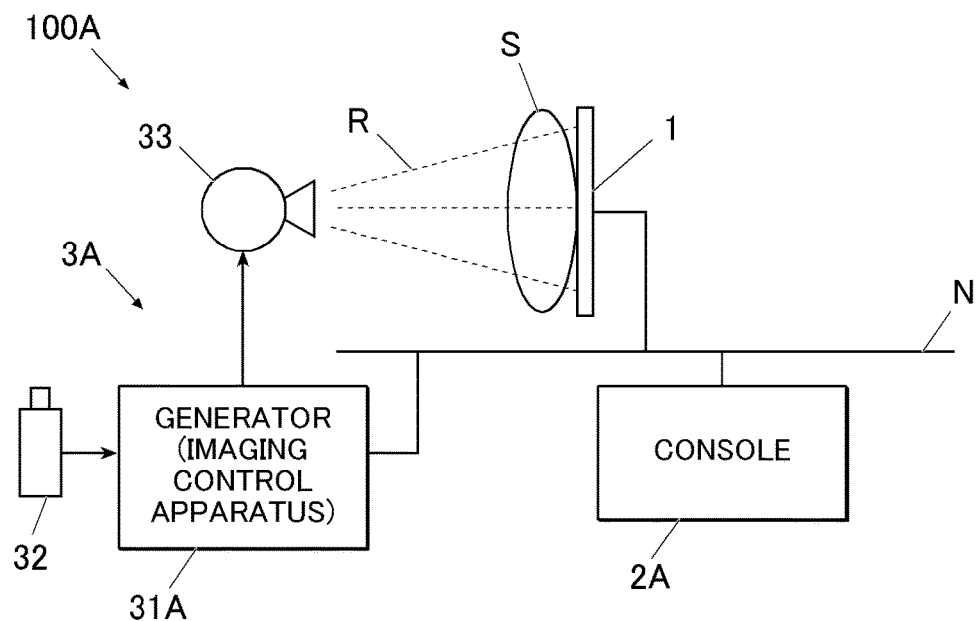
FIG. 3 is a block diagram of another example of a radiation imaging system according to the same embodiment.

Specifically, as shown in FIG. 3, for example, the radiation imaging system (hereinafter referred to as a "system 100A") may include, in addition to the above detector 1, a console 2A that does not have an imaging control function, and a generating apparatus 3A having a generator 31A that also serves as an imaging control apparatus.

The imaging control apparatus may also be provided independently.

Figure 4:
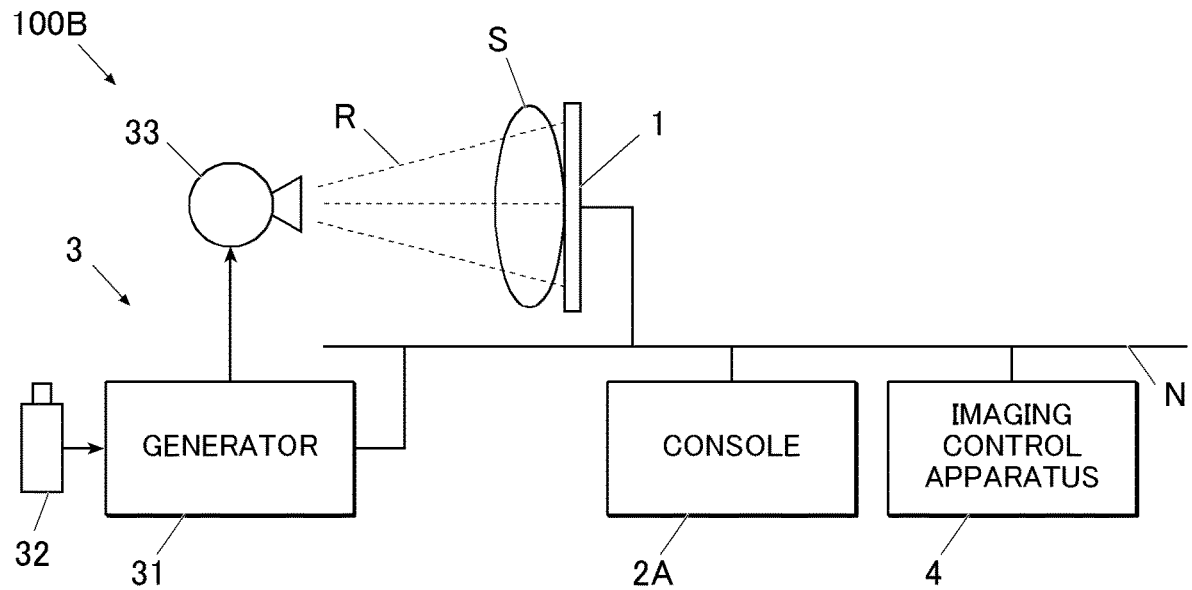
FIG. 4 is a block diagram of another example of a radiation imaging system according to the same embodiment.

Specifically, as shown in FIG. 4, for example, the radiation imaging system (hereinafter referred to as a "system 100B") may include, in addition to the above detector 1 and generating apparatus 3, a console 2A that does not have an imaging control function, and an imaging control apparatus 4.

2. Details of Imaging Control Apparatus

Next, details of the imaging control apparatuses (console 2, generator 31A, imaging control apparatus 4) included in the above system 100, 100A, 100B will be explained using the console 2, which also serves as the imaging control apparatus, as an example.

Figure 5:
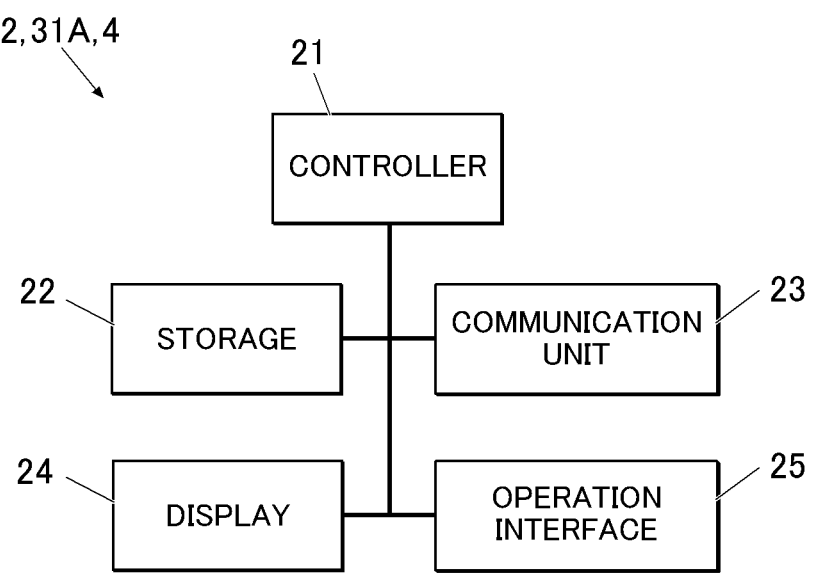
FIG. 5 is a block diagram showing an imaging control apparatus of the radiation imaging system of FIG. 1, FIG. 3, and FIG. 4.
Figure 6:
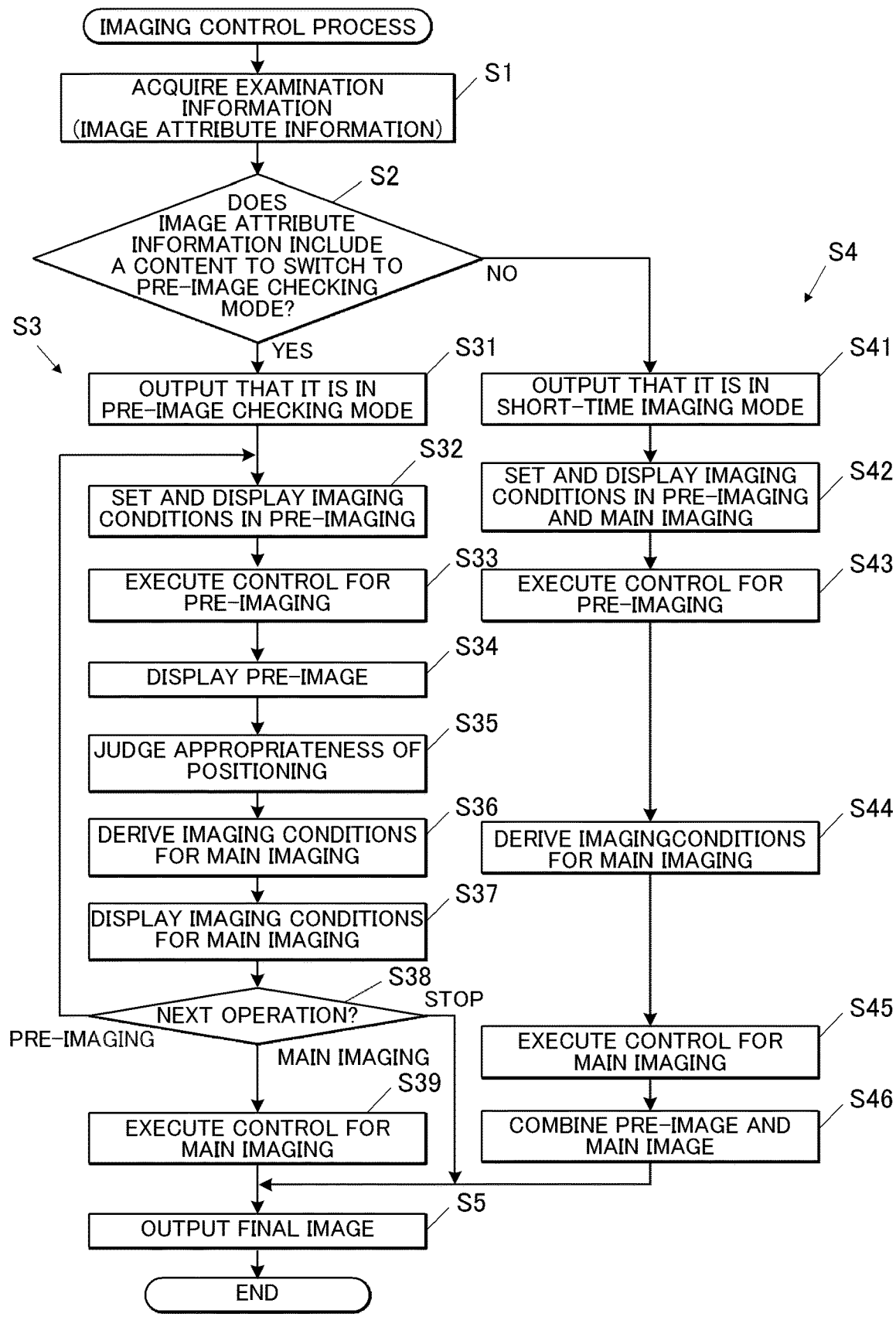
FIG. 6 is a flowchart showing steps of imaging control process executed by the imaging control apparatus of FIG. 5.

FIG. 5 is a block diagram showing the imaging control apparatus 2, 31A, 4, and FIG. 6 is a flowchart showing a flow of an imaging control process executed by the imaging control apparatus 2, 31A, 4.

[2-1. Configuration of Imaging Control Apparatus]

The console 2, which also serves as the imaging control apparatus, includes a controller 21, a storage 22, a communication unit 23, a display 24, and an operation interface 25, as shown in FIG. 5.

Respective components 21 to 25 are electrically connected to each other by a bus or the like.

The controller 21 is configured with a central processing unit (CPU), a random access memory (RAM), and the like.

The CPU of the controller 21 reads various programs stored in the storage 22 to load the programs in the RAM, executes various processes according to the loaded programs, and centrally controls the operation of each component of the console 2.

The storage 22 is configured with a non-volatile memory, a hard disk, and the like.

In addition, the storage 22 stores various programs executed by the controller 21, parameters necessary for executing the programs, and the like.

The storage 22 may be capable of storing image data of a radiation image acquired from another device.

The communication unit 23 is configured with a communication module and the like.

The communication unit 23 is connected to another device (the detector 1, the generating apparatus 3, and the like) by wire or wirelessly via a communication network N (local area network (LAN), wide area network (WAN), the Internet, or the like) to transmit and receive various signals, various data, or the like.

The display 24 is configured with, for example, a liquid crystal display (LCD), a cathode ray tube (CRT), or the like.

The display 24 displays a radiation image or the like corresponding to the image signal received from the controller 21.

The operation interface 25 is configured to be operated by the user.

The operation interface 25 includes a key board (a cursor key, number input keys, various function keys, and the like), a pointing device (mouse or the like), a touch panel stacked on the surface of the display 24, and the like.

The operation interface 25 outputs a control signal corresponding to the operation executed by the user to the controller 21.

The console 2 may not be provided with the display 24 and the operation interface 25, but receive a control signal from an input device provided separately from the console 2 via, for example, the communication unit 23 or the like, or output an image signal to a display device (monitor) provided separately from the console 2.

In addition, when another device (generating apparatus 3 or the like) is provided with a display and an operation interface, a control signal may be allowed to be received from the operation interface of the other device, or an image signal may be allowed to be output to the display of the other device (the display and the operation interface may be shared with other device).

[2-2. Operation of Imaging Control Apparatus]

Tire controller 21 of the console 2 configured as described above executes, for example, the imaging control process as shown in FIG. 6, when a predetermined condition is satisfied.

The predetermined conditions include, for example, turning the console 2 on, receiving a predetermined control signal from another device, executing a predetermined operation on the operation interface 25, and the like.

[2-2-1. Acquisition Process]

In this imaging control process, the controller 21 first executes an acquisition process (step S1).

In the acquisition process, the controller 21 acquires examination information.

In the acquisition process of the present embodiment, the controller 21 receives examination information from another system via the communication unit 23.

[2-2-2. Mode Switching Process]

After acquiring the examination information the controller 21 executes a mode switching process (Step S2).

In this mode switching process, the controller 21 switches its control mode to a pre-image checking mode or a short-time imaging mode.

The "pre-image checking mode" is a control mode in which the pre-image is displayed after the pre-imaging.

The "short-time imaging mode" is a control mode in which the main imaging is executed without displaying the pre-image after the pre-imaging.

In the mode switching process, the controller 21 automatically switches the control mode of the imaging control means based on image attribute information.

The "image attribute information" is included in the examination information and includes at least one of the followings:
- imaging technique information (imaging site, imaging (irradiation) direction, and the like)
- subject attribute information (disease, disability, age, body type, implants, attachments, and the like)
- radiographer (user) information (information on radiographic experience, number of radiographers)
- imaging purpose and place information (emergency, medical rounds, surgery, ICU, and the like)
- usage device information (movable examination car, general imaging device, and the like)

In the mode switching process of the present embodiment, the controller 21 switches the control mode to the one corresponding to the image attribute information included in the acquired examination reformation, using, for example, a mode decision table $T_1$ as shown in FIG. 7 indicating a correspondence between the imaging attribute information and the control mode.

Specifically, if the imaging attribute information includes the content to switch to the pre-image checking mode (Step S2: Yes), the controller 21 switches the control mode to the pre-image checking mode.

On the other hand, if the imaging attribute information docs not include the content to switch the control mode to the pre-image checking mode, that is, the content is to switch the control mode to the short-time imaging mode (Step S2: No), the controller 21 snitches the control mode to the short-time imaging mode.

This eliminates the need to select the control mode each time the examination is executed, and thus makes the system 100 more user-friendly.

When the control mode is switched based on the imaging technique information, imaging that involves difficult positioning can be executed in the pre-image checking mode. This can prevent imaging failures and prevent the subject S from being unnecessarily exposed to radiation.

Imaging that involves no difficult positioning is executed in the short-time imaging mode. This can shorten the time between the completion of pre-imaging and the start of main imaging, and reduce imaging failures due to body movements of the subject S.

Alternatively, when the control mode is switched based on the subject attribute information, imaging for which calculation of the imaging conditions (main dose and the like) for main imaging is difficult with high accuracy due to an attachment (implant, cast, and the like) of the subject S's, for example, can be executed in the pre-image checking mode. In this way, it is possible to check and optimize the main dose before the main imaging.

For example, elderly people tend to have difficulties in maintaining positioning. Therefore, if the subject S is older than a predetermined age, the pre-image checking mode can be used to prevent imaging failure and to prevent the subject S from unnecessary exposure to radiation.

Alternatively, when the control mode is switched based on the radiographer information, the imaging place information, or the usage device Information, imaging in situations that often result in retaking of images can be executed in the pre-image checking mode (in situations where the user is inexperienced, there are only a few radiographers, or there are a lot of obstacles (tubes, etc.) in the imaging place such as ICU, and the like). Then, it is possible to prevent imaging failure and to prevent the subject S from unnecessary exposure to radiation.

It is generally said that positioning is more difficult in a movable examination car than in a general radiography room. Therefore, for example, while chest imaging is executed in the pre-image checking mode in the movable examination car according to the usage dev ice information, similar chest imaging is executed in the short-time imaging mode in a general radiography room according to the usage device information. This can increase examination efficiency by preventing imaging failures in the movable examination car and by shortening the time required for imaging in the general radiography room.

Alternatively, the control mode may be switched based on a combination of two or more of the followings: the imaging technique information, the subject attribute information, the radiographer information, the imaging purpose and place information, and the usage device information.

For example, based on a combination of the subject attribute information and the radiographer information, if the subject S is older than a predetermined age (elderly) and there is only one radiographer, the pre-image checking mode is selected.

If the subject S is not elderly or if there are a plurality of radiographers, the short-time imaging mode is selected.

When there is more than one radiographers, the positioning of even an elderly subject S can be stabilized by being supported during imaging, thus results in less failures due to positioning. Therefore, when there is more than one radiographers, the short-time imaging mode can be selected to complete the imaging in a short time, thereby shortening the time to support positioning and reducing the physical burden on the radiographer(s).

In this mode switching process, the controller 21 may switch the control mode of the imaging control means based on operations executed on the operation interface 25 by the user.

When the subject S who has difficulty in suppressing tremor (such as a patient with symptoms such as tremor, a child) is imaged in the pre-image checking mode, the positioning may change between the pre-imaging and the main imaging alter checking of the positioning, and this causes an imaging failure. Since the pre-image does not help improve the quality of imaging in such a case, the subject S is uselessly and unnecessarily irradiated with radiation of the pre-dose.

In addition, when the subject S is imaged in the short-time imaging mode, even though the time between the completion of the pre-imaging and the start of the main imaging is shorter than in the pre-image checking mode, the body movement of the subject S may make it difficult to combine the pre-image and the main image, and retaking may be necessary.

Therefore, in the mode switching process, the controller 21 may switch to one of the following control modes based on the above-mentioned imaging attribute information: the pre-image checking mode, the short-time imaging mode, and the normal imaging mode in which the main imaging is executed at the beginning without executing pre-imaging.

In this way, it is possible to reduce the possibility of such imaging failures and prevent the subject from being unnecessarily exposed to radiation.

In addition, if imaging of subject S, who is in at least one of the stales of having an implant m the body or wearing a specific attachment such as a cast, is executed in the normal imaging mode, the process of calculating imaging conditions (main dose and the like) for the main imaging is omitted. Therefore, it is possible to prevent the main imaging from being executed under imaging conditions that are derived with low accuracy due to the presence of an implant or an attachment, which may result in an imaging failure.

By executing the mode switching process described above, the controller 21 serves as a mode switching means.

In addition, the process of executing the mode switching process is the mode switching step in the radiation imaging method using the system 100.

When automating the switching of the control mode for imaging in cases where the combination of various types of imaging attribute information are rarely used, it is necessary to store the sorting for many types of imaging attribute information, which requires an enormous time and effort when installing the system 100.

Therefore, after executing the mode switching process, the controller 21 may be able to overwrite the various settings in the switched control mode with new ones based on the operations executed on the operation interface 25 by the user.

In this way, by automating the switching of control modes roughly (so that most cases are applicable) and allowing the user to change only minimum settings for rare cases, the system 100 can be installed with reduced effort while still being able to execute imaging in rare cases.

[2-2-3. First Imaging Control Process]

When switching the control mode to the pre-image checking mode in the mode switching process, the controller 21 executes a first imaging control process (Step S3).

In other words, executing the first imaging control process is the sane as executing control in the pre-image checking mode (First Output Process)

In the first imaging control process, the controller 21 first executes the first output process (step S31).

In this first output process, the controller 21 outputs whether it is controlling in the pre-image checking mode or in the short-time imaging mode, in this case, the controller 21 outputs the fact that it is controlling in the pre-image checking mode.

In the first output process according to the present embodiment, the controller 21 causes the display 24 to display the fact that it is controlling in the pre-image checking mode.

In the first output process according to the present embodiment, the controller 21 transmits a signal to other devices (generating apparatus 3, or the like) indicating that it is controlling in the pre-image checking mode.

In the first output processing according to the present embodiment, the controller 21 continues this output at least until the main imaging is completed.

In control in the pre-image checking mode, the controller 21 display s a content that informs the user that pre- and main imaging are separately executed.

For example, as shown in FIG. 8A, two icons I corresponding to the number of imaging operations (the number of images displayed) are displayed.

The two icons I may be displayed so as to overlap, as shown in FIG. 8B.

Alternatively, the two icons I may be displayed with an interval between them, as shown in FIG. 8C.

As a result, the user can easily recognize that at least two imaging operations (pressing the first and second buttons of the irradiating instruction switch 32) are required alter this. Also, the user can easily recognize that two images (pre-image and main image) will be displayed during the series of imaging.

In this first output process, the controller 21 may output the fact that the control is being executed in the pre-image checking mode by sound, light, and the like.

When there are two control modes as in the case of the console 2 according to the present embodiment but the control mode is not output the user may misunderstand which control mode is used and stop the imaging in the middle.

For example, if the user mistakenly believes that the control mode is the short-time imaging mode though the imaging is actually being executed in the pre-image checking mode, the user may mistake the display of the pre-image as the completion of the main imaging, and may terminate the series of imaging without the main imaging. Since the series of imaging has to be executed again from the beginning in such a case, the subject S is uselessly and unnecessarily irradiated with radiation of the pre-dose.

However, by outputting information on which control mode is in use, it is possible to prevent the user from making a mistake.

(Pre-Imaging Condition Setting and Display Process)

After switching the control mode, the controller 21 executes the pre-imaging condition setting and display process (Step S32).

In this pre-imaging condition setting and display process, the controller 21 sets the imaging conditions for pre-imaging.

In the pre-imaging condition setting and display process, the controller 21 may be able to change the tube voltage value, tube current value, and irradiation time, or the tube voltage value and a product of tube current and time in the pre-imaging, based on the operations executed on the operation interface 25 by the user.

In the pre-imaging condition setting and display process, the controller 21 causes the display 24 to display one of the following values before the pre-imaging is executed.

the tube voltage, the tube current value, and the irradiation time when the pre-imaging is executed the tube voltage, and the product of tube current and time when the pre-imaging is executed (First Pre-Imaging Process)

After setting the imaging conditions for the pre-imaging, the controller 21 executes the first pre-imaging process (Step S33).

In this first pre-imaging process, the controller 21 executes control for the pre-imaging.

In this first pre-imaging process, the controller 21 first waits for the communication unit 23 to receive a signal indicating that the irradiating instruction switch 32 has been operated from the generator 31 of the generating apparatus 3.

Then, when the communication unit 23 receives a signal from the generator 31 that both the first and second buttons of the irradiating instruction switch 32 have been pressed, the controller 21 executes control to execute the pre-imaging. (For example, the controller 21 causes the communication unit 23 to transmit a signal to the detector 1 indicating the start of charge storage and readout.)

(Pre-Image Display Process)

After the pre-imaging, the controller 21 executes a pre-image display process (Step S34).

In this pre-image display process, the controller 21 causes the display 24 to display the pre-image based on the pre-image data received from the detector 1.

(Positioning Judgment Process)

After the pre-imaging, the controller 21 executes a positioning judgment process (step S35).

In this positioning judgment process, the controller 21 judges whether or not the positioning of the subject S is appropriate.

In the positioning judgment process of the present embodiment the controller 21 first acquires a pre-image from the detector 1.

After acquiring the pre-image, the controller 21 analyzes the pre-image.

After analyzing the pre-image, the controller 21 judges whether or not the positioning is appropriate based on the analysis results of the pre-image.

For the analysis of the pre-image and the judgment of the appropriateness of positioning, conventionally known techniques can be used.

By executing the positioning judgment process described above, the controller 21 serves as an analysis means and a positioning judgment means.

In this positioning judgment process, the controller 21 may not analyze the pre-image, but acquire analysis results from an analysis device that is not shown in the drawings.

Alternatively, the controller 21 may be able to set whether or not to execute this positioning judgment process before executing the process.

In this case, the controller 21 may set whether or not to execute the process based on the operation executed on the operation interface 25 by the user.

In such a case, the automatic judgment of the appropriateness of positioning is not executed when the judgment of the appropriateness of positioning must be compromised for reasons such as the physical characteristics of subject S. This allows the user to avoid the task of checking the result of the automatic judgment.

Alternatively, the controller 21 may automatically set whether or not to execute the process based on the imaging attribute information, for example, in a mode switching process.

The appropriateness of positioning is judged based on different criteria depending on the imaging technique. In addition, depending on the imaging technique, it may be difficult to automatically judge the appropriateness of positioning. However, because the appropriateness of positioning is not judged automatically in such cases, it is possible to prevent the user from being confused or from having to execute unnecessary checking due to incorrect judgment results.

Alternatively, if there is a positioning error that must be absolutely avoided in relation to the imaging technique, an automatic judgment of the suitability of positioning may be executed. This can ensure a quality of imaging above a certain level even when an inexperienced user executes the imaging (First Condition Derivation Process)

After executing the pre-imaging, the controller 21 executes the first condition derivation process (Step S36).

In this first condition derivation process, the controller 21 derives the imaging conditions for the main imaging based on the pre-image acquired in the pre-imaging.

In the first condition derivation process according to the present embodiment, the controller 21 derives the imaging conditions such that the pixels of the radiation image that is finally generated with radiation of only the main dose have desired density, that is, the imaging conditions on the premise that images are not assumed to be combined.

This is because the time from the end of the pre-imaging to the start of the main imaging is longer in the pre-image checking mode, during which the subject S moves relatively more largely, and this makes it difficult to combine the pre-image and the main image (the possibility of an imaging failure increases).

In the first condition derivation process (from the end of pre-imaging to the start of main imaging), the controller 21 may be able to change the tube voltage, the tide current value, and the irradiation time, or the tube voltage, and the product of tube current and time when the main imaging is executed based on the operations executed on the operation interface 25 by the user.

In this way, even if inappropriate imaging conditions are automatically derived due to the presence of implants, or the like, it is possible to prevent imaging failures by optimizing the conditions.

(Main Imaging Condition Display Process)

After deriving the imaging conditions for the main imaging, the controller 21 executes the main imaging condition display process (Step S37).

In the main imaging condition display process, the controller 21 causes the display 24 to display one of the following values before the main imaging is executed.

the tube voltage, the tube current value, and the irradiation time when the main imaging is executed the tube voltage, and the limit value of product of tube current and time when the main imaging is executed Thus, m the first imaging control process, controller 21 causes the imaging conditions for the pre-imaging and the imaging conditions for the main imaging to be displayed separately (when the imaging conditions for the pre-imaging are displayed, the imaging conditions for the main imaging are not displayed).

In the pre-image checking mode, a clearly defined user operation (for example, selection of the next operation to be executed as described below) is executed from the end of the pre-imaging to the start of the main imaging. Therefore, by separately displaying the imaging conditions for the pre-imaging and the imaging conditions for the main imaging, the display of the imaging conditions is linked to the user's operation, and the user can easily understand which imaging is about to be executed.

If the tube voltage value and the like is configured to be changed based on the user's operation in at least one of the processes of deriving the first condition and the pre-imaging condition setting and display process above, the controller 21 may be configured, upon changing one of the values for pre-imaging and main imaging, to automatically change the other one to the same value for parameters that must have the sane value for both pre-imaging and main imaging (for example, tube voltage, tube current, additive filters, and the like). Alternatively, if the pre-imaging Ins already been executed, the parameters may not be changeable in main imaging.

In this way, it is possible to prevent imaging failures caused by accidentally changing only one of the parameters for pre-imaging and main imaging, which must be set to the same value.

Also, in the first imaging control process, the controller 21 may simultaneously display the imaging conditions of the pre-imaging and the main imaging before the pre-imaging is executed.

In this case, the controller 21 may change the display method of at least one of the imaging conditions of the pre-imaging and main imaging before starting the imaging. The controller 21 may, for example, change the imaging condition of the next imaging so as to stand out more prominently than the imaging condition of the other imaging, or may change the imaging condition of the other imaging so as to stand out less prominently than the imaging condition of the text imaging.

Specifically, the imaging conditions for next imaging are displayed in a dark color or in a large size, or the imaging conditions for the other imaging are grayed out or displayed in a small size.

In this case, as the imaging conditions for main imaging, the controller 21 display s respective upper limits of the tube voltage value, the tube current value, and the irradiation time for the main imaging, or respective upper limits of the tube voltage value and a product of the tube current and the time for the main imaging.

When the imaging to be executed next is the main imaging, that is, when the pre-imaging has already been completed, the controller 21 may terminate the display of the imaging conditions for the pre-imaging after the pre-imaging.

Alternatively, in the above configuration, the controller 21 may display a single value for the imaging conditions (e.g., tube voltage, etc.) common to both the pre-imaging and main imaging.

(Operation Decision Process)

After displaying the imaging conditions for the main imaging on the display 24, the controller 21 executes the operation decision process (Step S38).

In this operation decision process, the controller 21 decides the next operation to be executed.

In the operation decision process according to the present embodiment, the controller 21 first waits for a predetermined period of time until at least one of the irradiating instruction switch 32 and the operation interface of the console 2 (for example, a touch panel type selection button provided on the display 24) is operated by the user.

When the user operates at least one of the irradiating instruction switch 32 and the operation interface 25, the controller 21 decides the next operation to be executed based on these operations.

Specifically, when the irradiating instruction switch 32 is operated in any of the followings, the controller 21 decides that the next operation to be executed is the completion of imaging
- in a case where all the buttons of the irradiating instruction switch 32 are released
- in a case where the second button is released before a predetermined period of time has elapsed since the end of the pre-imaging or the display of the pre-image
- in a case where, while all buttons are released, the operation interface 25 is operated to select completion of imaging Alternatively, when the irradiating instruction switch 32 is operated in any of the followings, the controller 21 decides that the next operation to be executed is the main imaging.
- in a case where, while only the second button of the irradiating instruction switch 32 is released (only the first button is pressed), the second button is pressed again
- in a case where the second button continues to be pressed for a predetermined period of time since the end of the pre-imaging or the display of the pre-image
- in a case where, while all buttons are released and the operation interface 25 is operated to select no operations, the second button is pressed again Alternatively, when the irradiating instruction switch 32 is operated in any of the followings, the controller 21 decides that the next operation to be executed is the pre-imaging.
- in a case where, while all the buttons of the irradiating instruction switch 32 are released, both the first and the second buttons are pressed again
- in a case where, while only the second button is released before a predetermined period of time has elapsed since the end of the pre-imaging or the display of the pre-image, the second button is pressed again
- in a case where, while all buttons are released and the operation interface 25 is operated to select the pre-imaging, the second button is pressed again If the next operation to be executed is decided to be the pre-imaging in this operation decision process, the controller 21 returns to the pre-imaging condition setting and display process (Step S32).

If, on the other hand, the next operation to be executed is decided to be the completion of imaging in the operation decision process, the controller 21 proceeds to the process of step S5.

In the operation decision process, the controller 21 may cause the display 24 to display, for example, a message indicating the start of the operation decision process, the choice of the next operation to be executed (main imaging, pre-imaging, or completion of imaging), the selected next operation, and the like (First Main Imaging Process)

When the next operation to be executed is decided to be the main imaging in the above operation decision process, the controller 21 executes the first main imaging process (Step S39).

In this first main imaging process, the controller 21 first waits for the communication unit 23 to receive a signal indicating that the irradiating instruction switch 32 has been operated from the generator 31 of the generating apparatus 3.

Then, when the communication unit 23 receives a signal from the generator 31 that both the first and second buttons of the irradiating instruction switch 32 have been pressed, the controller 21 executes control to execute the main imaging (For example, the controller 21 causes the communication unit 23 to transmit a signal to the detector 1 indicating the start of charge storage and readout.)

In the first main imaging process, the controller 21 may control (to take moving images, for example) such that the radiation emission by the generating apparatus 3 and the image generation by the detector 1 are repeated several times in executing the main imaging once.

(First Situation Transmission Process)

In the first imaging control process, the controller 21 executes the first situation transmission process in parallel with the above processes of steps S33 to S39.

In this first situation transmission process, the controller 21 causes a situation transmitter to transmit different contents between the period from the end of pre-imaging to the start of main imaging and the period during pre-imaging or main imaging.

Figure 9A:
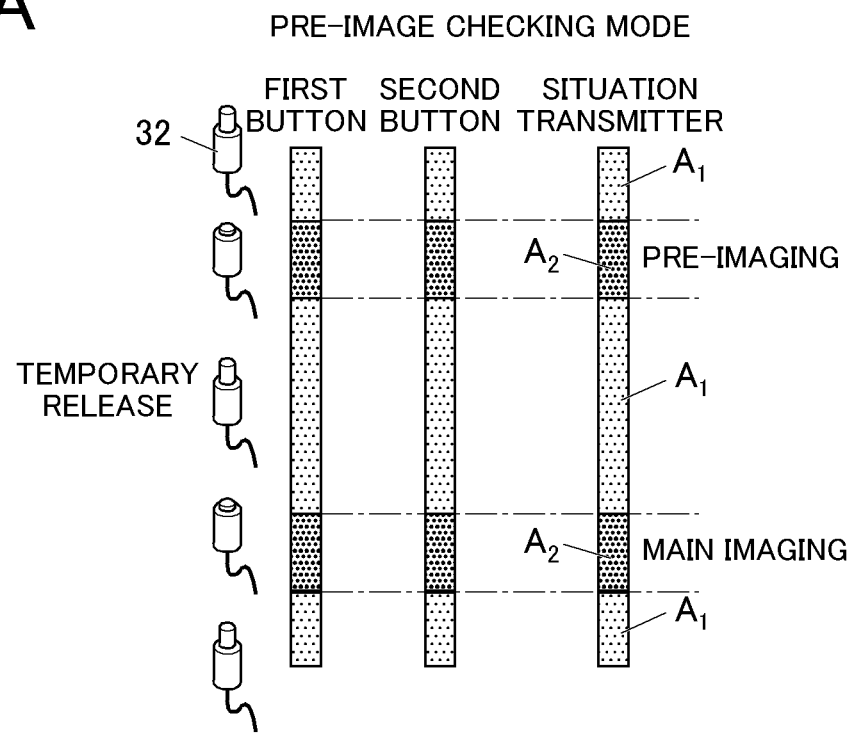
FIG. 9A is a diagram that shows changes in the situation transmitter of the radiation imaging system of FIG. 1, FIG. 3, and FIG. 4 along with proceedings of imaging.

Specifically, for example, as shown in FIG. 9A, the controller 21 sets the situation transmitter to be in a first mode A1 while neither the pre-imaging nor the main imaging is being executed, and sets the situation transmitter to be in a second mode A2 while the pre-imaging or the main imaging is being executed.

In FIG. 9A, the situation transmitter is set to be m the same first mode A1 before the pre-imaging, after the pre-imaging and before the start of the main imaging, and after the main imaging. However, the situation transmitter may be in different modes in these three periods as long as it is different from the second mode A2.

Examples of the situation transmitter include the display 24, a monitor externally attached to the imaging control apparatus, an irradiating instruction switch 32, a speaker, a lamp, and the like.

As a result in the pre-image checking mode, the user can intuitively understand that the button of the irradiating instruction switch 32 needs to be released for the time being.

In particular, if the irradiating instruction switch 32 functions as the situation transmitter, the user can be aware of the current situation (whether or not imaging is being executed) at hand.

Thus, pre-imaging may be executed twice or more, or main imaging may not be executed in the first imaging control process (pre-image checking mode), depending on the user's choice. Therefore, the actual radiation dose until the final image is obtained is calculated by "(pre-dose)×(number of pre-imaging)+(main dose)" or "(pre-dose)×(number of pre-imaging)" (when main imaging is not executed)

[2-2-4. Second Imaging Control Process]

When switching the control mode to the short-time imaging mode in the mode switching process (Step S2), the controller 21 executes a second imaging control process (Step S4).

In other words, executing the second imaging control process is the sane as executing control in the short-time imaging mode (Second Output Process)

In the second imaging control process, the controller 21 first executes the second output process (step S41).

In the second imaging control process, the controller 21 outputs the fact that it is controlling in the short-time imaging mode.

In the second output process according to the present embodiment, the controller 21 causes the display 24 to display the fact that it is controlling in the short-time imaging mode.

In the second output process according to the present embodiment, the controller 21 transmits a signal to other devices (generating apparatus 3, or the like) indicating that it is controlling in the short-time imaging mode.

In the second output processing according to the present embodiment, the controller 21 continues this output at least until the main imaging is completed.

In the second output process, the controller 21 displays a content telling the user that pre-imaging and main imaging are executed not separately but as a series of imaging, or a content that does not make the user aware that pre-imaging and main imaging are separately executed.

For example, the controller 21 displays one icon I corresponding to the number of imaging operations (the number of images displayed), as shown in FIG. 8D.

If two icons I (FIG. 8A and FIG. 8C) are set to be displayed without being overlapped, in the above first output process, the controller 21 may display two overlapped icons I in this second output process as shown in FIG. 8B.

This makes it easier for the user to understand that there will be one imaging operation to be executed afterwards and that a single image (a main image) will be displayed during the series of imaging.

In this second output process, the controller 21 may output the fact that the control is being executed in the short-time imaging mode by sound, light, and the like.

When there are two control modes as in the case of the console 2 according to the present embodiment but the control mode is not output, the user may misunderstand which control mode is used and stop the imaging in the middle.

For example, if the user mistakenly believes that the control mode is the pre-image checking mode though the imaging is actually being executed in the short-time imaging mode, the user may release the button of the irradiating instruction switch upon completion of the pre-imaging and terminate the series of imaging. Also, if the user finds that main imaging has not been executed after a long time that main imaging has not been executed and executes main imaging, the subject S may have moved significantly, thereby making it difficult to combine the pre-image and the main image. Also in such cases, the subject S is uselessly and unnecessarily irradiated with radiation of the pre-dose. Alternatively, the user may mistakenly believes that the image displayed after the main imaging as the pre-image, and check and adjust the positioning of the subject S based on this mistake. These unnecessary operations may reduce the examination efficiency.

However, by outputting that the control is being executed in the short-time imaging mode, it is possible to prevent the user from making a mistake.

By executing the second output process or the first output process described above, the controller 21 serves as an outputting means or a mode notifying means.

In addition, the process of executing the first output process or the second output process is the mode notifying step in the radiation imaging method.

(Imaging Condition Setting and Display Process)

After switching the control mode, the controller 21 executes an imaging condition setting and display-process (Step S42).

In this imaging condition setting and display process, the controller 21 sets the imaging conditions for pre-imaging.

Also, in the imaging condition setting and display process, the controller 21 displays the tube voltage, tube current, and irradiation time, or the product of tube current and time.

In the imaging condition setting and display process according to the present embodiment, before the pre-imaging, the controller 21 displays: the values of tube voltage and tube current for the pre-imaging, the values of tube voltage and tube current for the main imaging, and the upper limit of the sum of the irradiation time for the pre-imaging and the irradiation time for the main imaging; or the value of tube voltage for the pre-imaging, the value of tube voltage for the main imaging, and the upper limit of the sum of the product of the tube current and the time for the pre-imaging and the product of the tube current and the time for the main imaging.

When the tube voltages are the sane for both the pre-imaging and main imaging, a single value may be displayed. In this way, the user needs to check less information, and can easily recognize the imaging conditions.

When the tube currents are also the sane for both the pre-imaging and main imaging, a single value may be displayed in the same way as the tube voltage.

Thus, while the controller 21 causes the imaging conditions for the pre-imaging and main imaging to be displayed separately in the above first imaging control process, the controller 21 causes them to be displayed together in the second imaging control process.

In the pre-image checking mode, a clearly defined user operation is executed between the pre-imaging and the main imaging, and the imaging conditions for the pre-imaging and main imaging are separately displayed in the first imaging control process. This allows the user to recognize that the imagings are executed separately, such that the display is linked to the user's operation, is easily understood, and can prevent misunderstanding of the mode.

Meanwhile, in the short-time imaging mode, no user operation is executed between the pre-imaging and the main imaging as detailed late, and the imaging conditions of pre-imaging and main imaging are displayed collectively as if they were a single imaging in the second imaging control process. As a result the display is linked to the user's operation, is easily understood, and can prevent misunderstanding of the mode.

By executing the imaging condition setting and display process described above, or the pre-imaging condition setting and display process and the main imaging condition display process in the first imaging control process described above, the controller 21 and the display 24 serve as a display means.

(Second Pre-Imaging Process)

After setting the imaging conditions for the pre-imaging, the controller 21 executes the second pre-imaging process (Step S43).

In this second pre-imaging process, the controller 21 executes control to execute the pre-imaging (Second Condition Derivation Process)

After executing the pre-imaging, the controller 21 executes a second condition derivation process (step S44).

In other words, in the second imaging control process, the controller 21 does not execute the positioning judgment process (does not judge the appropriateness of positioning) after the pre-imaging. This shortens the time between the end of the pre-imaging and the start of the main imaging, thereby reducing the body movement of the subject S during that time, so that the pre-image and the main image can be easily combined (the possibility of an imaging failure is reduced).

In this second condition derivation process, the controller 21 derives the imaging conditions for the main imaging based on the pre-image acquired in the pre-imaging.

In the second condition derivation process according to the present embodiment, the controller 21 derives the imaging conditions such that the pixels of the radiation image that is finally generated with radiation of the total dose of the pre-dose and the main dose have desired density.

In other words, while the controller 21 derives the imaging conditions without the assumption of image combination in the above first imaging control process, the controller 21 derives the imaging conditions with the assumption of image combination in the second imaging control process.

The total radiation dose of the subject S can be reduced by the amount of the pre-dose m this way, compared to when the first imaging control process is executed.

By executing the second condition derivation process described above, or the first condition derivation process in the above first imaging control process, the controller 214 serve as a condition derivation means.

(Second Main Imaging Process)

After deriving the imaging conditions for the main imaging, the controller 21 executes a second main imaging process (Step S45).

In this second main imaging process, the controller 21 automatically executes the main imaging.

In the second main imaging process, the controller 21 may control such that the radiation emission by the generating apparatus 3 and the image generation by the detector 1 are repeated several times in executing the main imaging once (Second Situation Transmission Process)

In the second imaging control process, the controller 21 executes the second situation transmission process in parallel with the above processes of steps S43 to S45.

In this second situation transmission process, the controller 21 causes the same content to be transmitted in the period from the end of the pre-imaging to the start of the main imaging as in the period during the pre-imaging or main imaging.

Figure 9B:
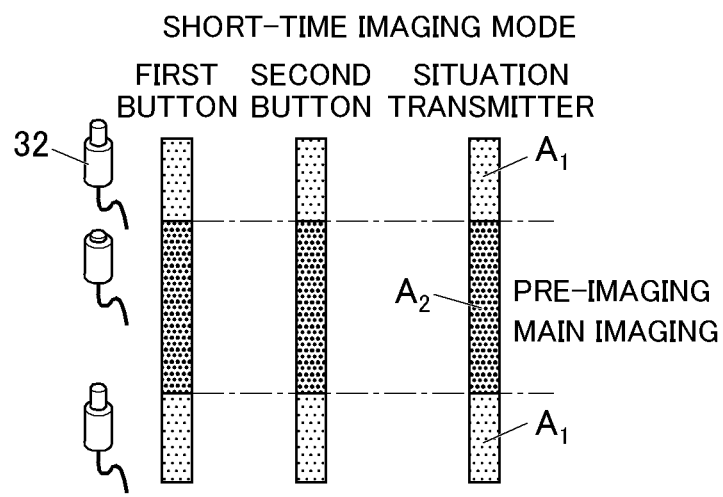
FIG. 9B is a diagram that shows changes in the situation transmitter of the radiation imaging system of FIG. 1, FIG. 3, and FIG. 4 along with proceedings of imaging.

Specifically, for example, as shown in FIG. 9B, the controller 21 sets the situation transmitter to be in a first mode A1 while neither the pre-imaging nor the main imaging is being executed, and sets the situation transmitter to be in a second mode A2 in the period from the start of the pre-imaging to the end the main imaging.

This will prevent the user from misunderstanding the end of the pre-imaging in the short-time imaging mode as the end of the main imaging and from releasing the button of the irradiating instruction switch 32.

By executing the second situation transmission process described above, or the first situation transmission process in the first imaging control process described above, the controller 21 and the display 24 serve as a situation transmission means.

(Combination Process)

After the main imaging, the controller 21 executes the combination process (Step S46).

In this combination process, the controller 21 generates a combination image by combining the pre-image and the main image acquired in the main imaging. Because the time between the end of the pre-imaging and the start of the main imaging is short in the short-time imaging mode and the body movement of the subject S is small during the time, the pre-image and the main image are suitable for the combination.

Images can be combined using a variety of previously known techniques.

By executing the combination process described above, the controller 21 serves as a combination means.

The controller 21 may be able to set whether or not to execute this combination process for each control mode before executing the process (at least one of the following timings: before the pre-imaging, before the main imaging, and alter the main imaging).

When the pre-image and main image are set not to be combined in such a configuration, the controller 21 may derive the imaging conditions such that the pixels of the radiation image that is finally generated by radiation of only the main dose have desired density, even when this second condition derivation process is executed (control is executed in the short-time imaging mode).

In such cases, the controller 21 serves as a setting means.

In some cases, depending on the imaging purpose, imaging technique, and the like (for example, when imaging microfractures), a non-combined image (for example, the main image) may be more appropriate for diagnosis than a combined image.

Also, depending on the doctor who ordered the imaging, the non-combined image may be preferred as the final image used for diagnosis.

Therefore, in such a configuration, the controller 21 may automatically set the control mode based on the imaging attribute information.

In this case, the controller 21 may overwrite and change the control mode set in response to an operation ("manually") made on the operation interface 25 by the user.

In this case, for example, the images are set to be combined by default, and the user can manually change the setting if necessary so that the images are not combined. In this way, it is possible to flexibly meet the needs of the doctor and the like without setting a detailed classification in advance.

In this way, since pre-imaging and main imaging are each executed once in the second imaging control process (short-time imaging mode), the actual radiation dose until the final image is obtained is calculated by "(pre-dose)+(main dose)."

[2-2-5. Final Image Display Process]

After the first imaging control process (Step S3) or the second imaging control process (Step S4), the controller 21 executes a final image display process (Step S5) as shown m FIG. 6.

In this final image display process, the controller 21 outputs the final image.

In the final image display process according to the present embodiment, the controller 21 causes the display 24 to display the final image.

The final image is a radiographic image that is finally generated just before this final image display process (just before the end of the imaging control process).

That is, if the first imaging control process is executed before this final image display process, the main image or the pre-image is the final image.

In other words, in the first imaging control process, the controller 21 does not execute the combination process (does not combine the pre-image with the main image) before displaying the final image. Because the time between the end of the pre-imaging and the start of the main imaging is long in the pre-image checking mode and the body movement of the subject S is large during the time, the pre-image and the main image are not suitable for the combination.

If the second imaging control process is executed before this final image display process, the combination image is the final image.

By executing the imaging control process described above, the controller 21 serves as an imaging control means.

[2-2-6. Others]

When the main imaging is started in spite of some abnormality occurring before the start of the main imaging, a main image that is not suitable for diagnosis may be acquired.

Therefore, in the above-mentioned imaging control process, the controller 21 may execute the mode switching process (switch its own control mode) after the pre-imaging.

Figure 10:
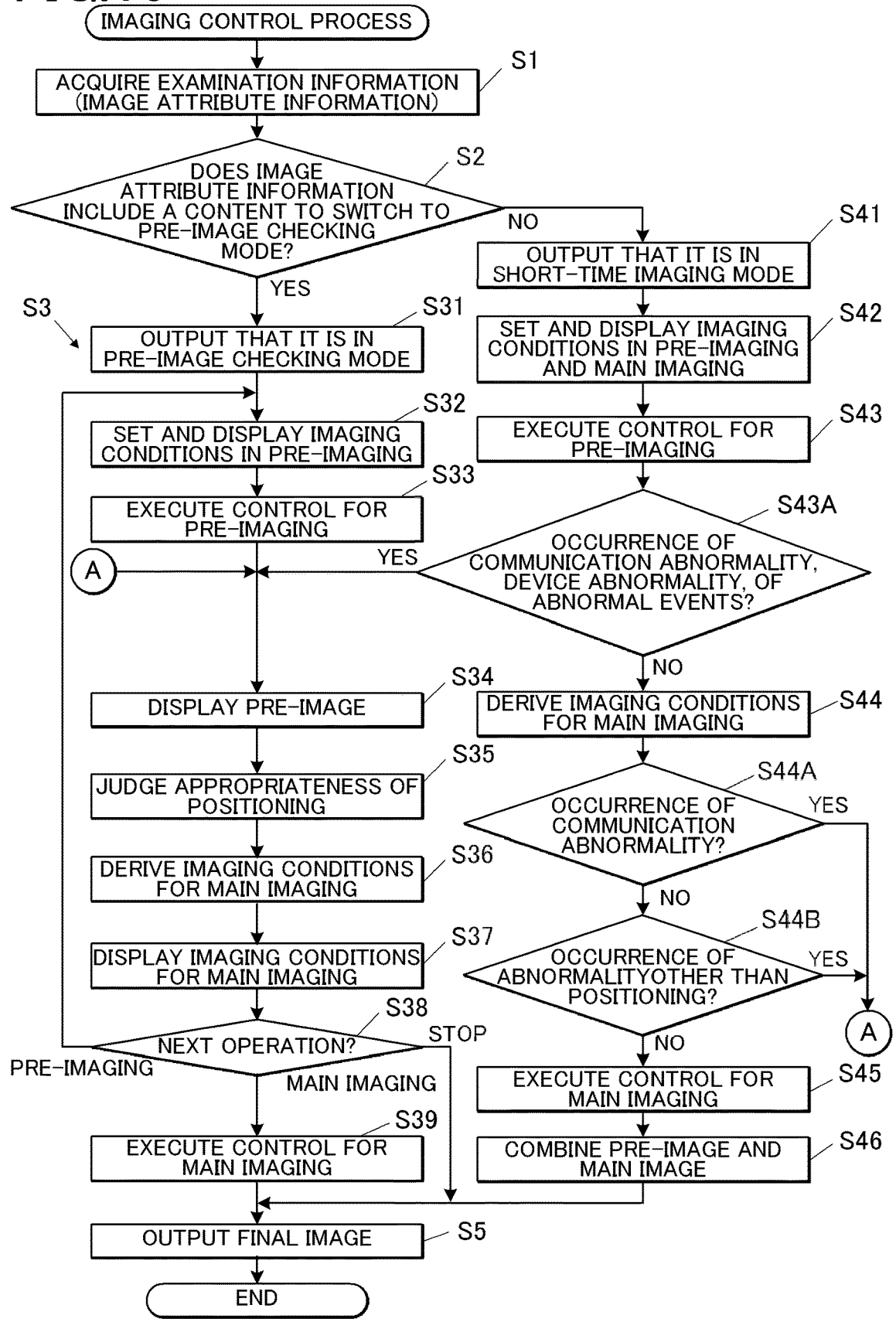
FIG. 10 is a flowchart slewing steps of imaging control process executed by the imaging control apparatus according to a modified example of the same embodiment.

Specifically, as shown in FIG. 10, for example, in the short-time imaging mode, the controller 21 may determine whether or not an abnormality has occurred during the period from the end of the pre-imaging to the start of the main imaging (steps S43A, S44A, S44B). If the controller 21 determines that an abnormality has occurred, the controller 21 may switch the control mode to the pre-image checking mode.

In this case, the controller 21 may determine whether or not an abnormality has occurred (switch the control mode) based on at least one of the following pre-imaging results.
determination of abnormality in density based on pre-image
artifact detection based on pre-image
determination of subject type based on pre-image.
communication abnormality detection or communication delay detection in pre-imaging
abnormality determination in the actual values of imaging conditions or irradiated pre-dose in pre-imaging
detection of abnormal operation or dev ice abnormality when pre-imaging is executed In this case, the controller 21 may determine whether or not an abnormality has occurred based on the results of processing in the positioning judgment process (step S35).

In such a case, the processing time can be shortened compared to the case where the process to obtain the above pre-imaging result for switching the control mode is executed separately from the second condition derivation process.

If it is determined that an abnormality has occurred after a pre-image is acquired in the second pre-imaging execution process, the controller 21 may execute the pre-image display process after switching to the pre-image checking mode. As a result, the user can easily understand the situation of the system 100.

In this case, in the operation decision process, the controller 21 may be able to select only the pre-imaging or the completion of imaging as the selectable next operation (the main imaging cannot be selected).

On the other hand, if it is determined that an abnormality (for example, a communication abnormality) has occurred when no pre-image has been acquired, the controller 21 may skip the processes from the pre-image display process to the main imaging condition display process after switching to the pre-image checking mode.

After switching from the short-time imaging mode to the pre-image checking mode, the controller 21 may derive the imaging conditions such that the pixels of the radiation image finally generated by radiation of only the main dose in the first condition derivation process have the desired density, and skip the combination process. This is because the time from the end of the pre-imaging to the start of the main imaging is longer due to the operation decision process after switching to the pre-image checking mode, the subject S moves relatively more largely and this makes it difficult to combine the pre-image and the main image.

If the control mode is switched to the pre-image checking mode after the second condition derivation process, the controller 21 may omit processes in the first condition derivation process to be executed after the switching that are common to the second condition derivation process and may use the processing results acquired in the second condition derivation process. As a result, the processing time can be shortened compared to the case where the first condition derivation process is executed entirely from the beginning.

After deriving the imaging conditions for the main imaging in the above imaging control process, the controller 21 of the console 2 may execute a determination process.

In this determination process, the controller 21 determines whether or not the derived imaging conditions for the main imaging satisfy a predetermined condition.

This "predetermined condition" includes, for example, that the tube current that has been set is above a predetermined value.

Then, the controller 21 causes the communication unit 23 to transmit the determination result to the generator 31 of the generating apparatus 3.

By executing the determination process described above, the controller 21 serves as a determination means.

3. DETAILS OF GENERATOR

Next, the details of the generators 31, 31A provided in the above systems 100, 100A, 100B will be explained using the generator 31, which does not serve as an imaging control apparatus, as an example.

Figure 11:
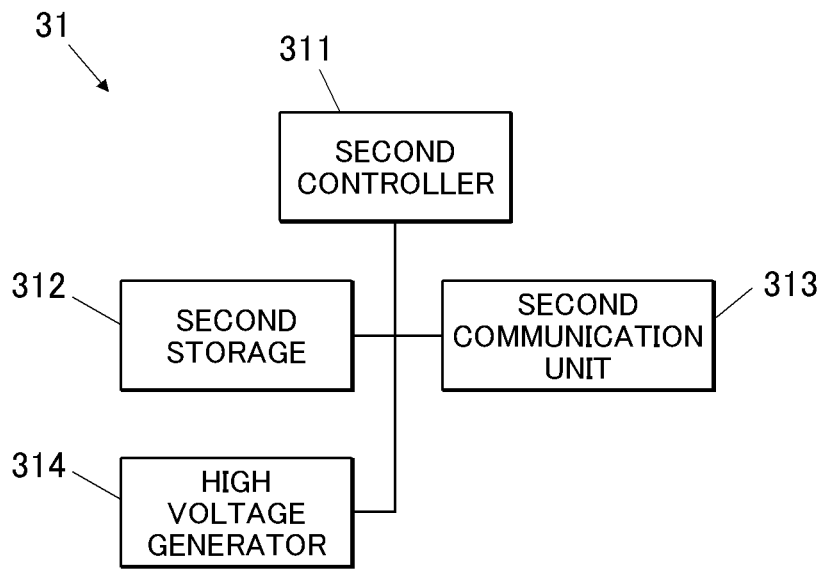
FIG. 11 is a block diagram slewing a generator of the radiation imaging system of FIG. 1.

FIG. 11 is a block diagram of the generator 31.

[3-1. Configuration of Generator]

As shown in FIG. 11, the generator 31 includes a second controller 311, a second storage 312, a second communication unit 313, and a high voltage generator 314.

All of these units 311 to 314 are electrically connected by bus or other means.

The second controller 311 is constituted by a CPU, RAM, and the like.

The CPU of the second controller 311 loads various programs stored in the second storage 312, expands them in the RAM, executes various processes according to the expanded programs, and centrally controls the operation of each unit of the generator 31.

The second storage 312 is constituted by non-volatile memory, hard disk, and the like.

In addition, the second storage stores various programs executed by the second controller 311, parameters necessary for executing the programs, and the like.

The second communication unit 313 is configured with a communication module and the like.

The second communication unit 313 is connected to another device (the detector 1, the console 2, and the like) by wire or wirelessly via a communication network N (local area network (LAN), wide area network (WAN), the Internet, or the like) to transmit and receive various signals, various data, or the like.

The high voltage generator 314 applies the tube voltage in response to the control signal received from the second controller 311 to the tubular bulb 33 and applies the tube current in response to the control signal to the tubular bulb 33.

[3-2. Operation of Generator]

The second controller 311 of the generator 31 configured as described above operates as follows.

For example, the second controller 311 executes the tubular bulb control process when predetermined condition is satisfied.

The predetermined conditions include, for example, turning the generator 31 on, receiving a predetermined control signal from another device, executing an operation on the irradiating instruction switch 32, and the like.

In the tubular bulb control process, the second controller 311 controls the state of the tubular bulb 33 based on the control mode of the console, the operation mode of the irradiating instruction switch 32, and the like.

Specifically, based on the signal that only the first button of the irradiating instruction switch 32 has been pressed, the second controller 311 first causes the second communication unit 313 to transmit a signal to the tubular bulb 33 instructing it to start preparing for irradiation of radiation R.

In the tubular bulb control process, based on the signal that the first and second buttons of the irradiating instruction switch 32 are both pressed, the second controller 311 causes the high voltage generator 314 to generate the tube voltage and tube current in response to the set imaging conditions. Then, the high voltage generator 314 applies the generated tube voltage to the tubular bulb 33 and applies the tube current to the tubular bulb 33.

In the tubular bulb control process, the second controller 311 determines before starting pre-imaging whether or not the signal received from the console 2 indicates that the control is in pre-image checking mode.

If it is determined that the signal indicates that control is being executed in the pre-image checking mode (controller 21 executes control in the pre-image checking mode), the second controller 311 temporarily cancels the irradiation-ready state of the tubular bulb 33 from the completion of the pre-imaging to the start of the main imaging.

In the pre-imaging checking mode, it is sometimes difficult to judge whether or not positioning is appropriate, and it may take time (about 10 to 20 seconds) to check the image.

If the irradiation-ready state of the tubular bulb 33 continues during this period, loads on the filament and the anode rotor increase, and the lifetime of the tubular bulb 33 is shortened. When the lifetime of the tubular bulb 33 is shortened, the maintenance cost of the generating apparatus 3 increases due to the replacement of the tubular bulb 33.

However, by temporarily canceling the irradiation-ready state of the tubular bulb 33, the lifetime of the tubular bulb 33 can be extended and the maintenance cost of the generating apparatus 3 can be reduced.

After canceling the irradiation-ready state of the tubular bulb 33, on receiving an instruction by the user to start the main imaging or to start the pre-imaging again, the second controller 311 causes the second communication unit 313 to transmit a signal to the tubular bulb 33 to instruct it to start the preparation for irradiation of radiation R.

If it is determined that the signal does not indicate that control is being executed in the pre-image checking mode (controller 21 executes control in the short-time imaging mode), the second controller 311 does not cancel the irradiation-ready state of the tubular bulb 33 from the end of the pre-imaging until the start of the main imaging.

In the short-time imaging mode, the time from the end of pre-imaging to the start of main imaging is desired to be as short as possible. At the same time, it generally takes about one to several seconds until the tubular bulb 33 is ready to generate radiation R. Therefore, when irradiation for radiation for main imaging is separately prepared after the pre-imaging, the time from the end of the pre-imaging to the start of the main imaging becomes longer, and during that time, the subject S may move relatively largely. This increases the risk that the pre-image and main image are difficult to be combined (the possibility of an imaging failure increases).

However, by not canceling but maintaining the irradiation-ready state of the tubular bulb 33, the risk of such an imaging failure can be reduced.

If the controller 21 of the console 2 is configured to execute the determination process and determines that the imaging conditions for the main imaging satisfy the predetermined conditions, the second controller 311 may not cancel the irradiation-ready state of the tubular bulb 33 in this tubular bulb control process even when the console 2 executes control in the pre-image checking mode.

For example, the irradiation-ready state may not be canceled when the tube current set by the console 2 is less than 500 mA, which is a small load, and may be canceled as usual when the tube current is 500 mA or more, which is a large load.

When radiation R of two different focal sizes (large and small) can be emitted, the irradiation-ready state may not be canceled when durability against high loads is relatively high because of the emission of radiation R with a large focus, and may be canceled as usual when durability against high loads is relatively low because of the emission of radiation R with a small focus. In this way, it is possible to balance extension of lifetime of the tubular bulb 33 and waiting time during imaging.

In the pre-image checking mode, the second controller 311 may set whether or not to continue the irradiation-ready state based on an operation executed by the user. In this way, it is possible to adapt to the desire of a user who wants to shorten the waiting time during imaging rather than extending the lifetime of the tubular bulb 33.

Alternatively, when the irradiation-ready state is canceled, the second controller 311 may cancel the irradiation-ready state of only one of the anode rotor and filament, while continuing the irradiation-ready state of the other. In this way, it is possible to extend the lifetime of one of the parts whose irradiation-ready state is canceled.

By executing the tubular bulb control process described above, the second controller 311 serves as a tubular bulb control means.

[3-2-2. Display Control]

When the controller 21 of the console 2 executes the pre-image display process, the second controller 311 causes the tubular bulb display 33a to display the pre-image based on the image data of the pre-image received from the console 2.

In this way, when positioning is executed again after the completion of pre-imaging, the user can consider the points to be corrected on the spot while referring to the pre-image displayed on the tubular bulb display 33a.

When pre-imaging is executed a plurality of times, the second controller 311 may display all the acquired pre-images.

Alternatively, in such a case, the second controller 311 may display not all the pre-images, but only the most recently acquired ones.

In this way, it is easier for the user to compare a plurality of pre-images to consider refinement of the positioning.

The second controller 311 of the above configuration may display a plurality of pre-images, for example, in a matrix, in a single vertical (up and down) row or a single horizontal (left and right) row, or in such a way that the most recent pre-image is larger than other pre-images acquired before it.

If there are several pre-images, the more recently obtained one in which the positioning of subject S is more optimized would be more helpful in refinement of the positioning. Therefore, by displaying the pre-images as described above, the more helpful images are more easily visible, and the efficiency of work during imaging can be improved.

In the configuration described above, the second controller 311 may select how to display the pre-images in response to the operation executed by the user on the tubular bulb operation interface (not shown in the drawings) provided on the tubular bulb 33.

Alternatively, the second controller 311 may switch between displaying and hiding a plurality of pre-images in response to a display switching operation of the pre-images displayed on the tubular bulb display 33a (for example, a flick operation executed on a touch panel laminated to the tubular bulb display 33a).

At that time, the second controller 311 may display, together with the pre-images P displayed on the tubular bulb display 33a, the order information according to the imaging order attached to the respective pre-images P.

Figure 12A:
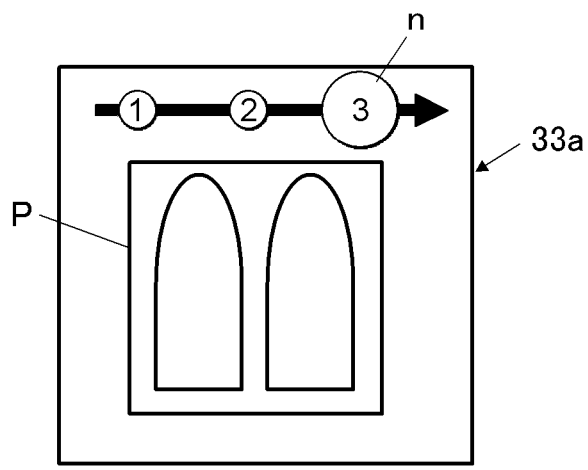
FIG. 12A is a diagram slewing a method of displaying a pre-image.
Figure 12B:
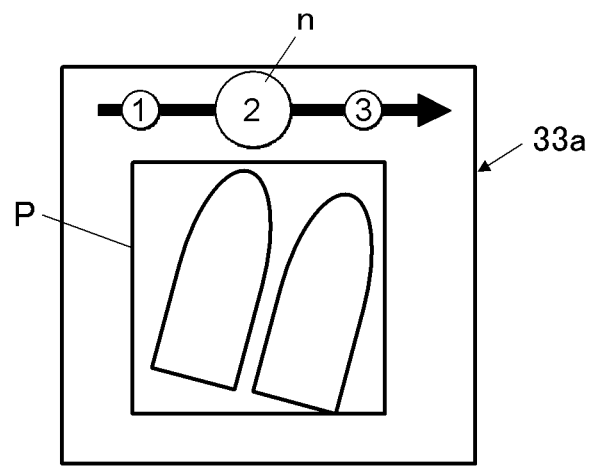
FIG. 12B is a diagram showing a method of displaying a pre-image.

This order information includes, for example, the number n indicating the imaging order as shown in FIG. 12A and FIG. 12B, as well as symbols other than the number n such as alphabets (A, B, C, and the like) that can be used to indicate the order, time information at the time of the imaging, and the like.

The time information includes, for example, information on the time when the respective pre-images P are taken, information indicating how many minutes before now the pre-images P were each taken, and information indicating how many minutes before the most recent pre-image P the pre-images P were each taken.

By indicating the order information together with the pre-image P in this way, it is possible to prevent the user from failing to see how the positioning adjustment has been made on the pre-image P being displayed.

When the console 2 executes the positioning judgment process, the second controller 311 may cause the tubular bulb display 33a to display the result of the judgment together with (for example, superimposing) the pre-image.

Specifically, if the console 2 determines that a lung field is missing in the positioning judgment process, for example, the second controller 311 generates an image of the missing part and displays it superimposed on the pre-image.

The second controller 311 may cause the tubular bulb display 33a to display the contents displayed on the display 24 during the operation decision process (step S38) by the console 2 (for example, indication that the operation decision process is to be started, the choices of the next operation to be executed (main imaging, pre-imaging, completion of imaging), the selected next operation, and the like). In this case, in response to operation of at least one of the irradiating instruction switch 32 and the tubular bulb operation interface (for example, a touch panel type selection button provided on the display 24, not shown in the drawings) of the tubular bulb 33, the second controller 311 can determine the next operation (main imaging, pre-imaging or completion of imaging) instead of the console 2 based on tire operation.

In this way, after reviewing the positioning, the user can select the next operation by simply operating the irradiating instruction switch 32 on the spot, without returning to the operation room to check the display content of the display 24 or operate the operation interface 25 of the console 2. As a result, the time from the completion of positioning to the next radiation irradiation can be shortened, and the risk of positioning shifts during that time can be minimized.

In executing the pre-imaging, the second controller 311 may cause a visible light camera (not shown in the drawings) of the tubular bulb 33 to take an image of an area that is irradiated with radiation R.

The visible light camera may be integrated with the housing of the tubular bulb 33, or may be attached to the tubular bulb 33 as a separate housing.

Alternatively, the visible light camera may be integrated with the housing of a collimator (not shown m the drawings) or may be attached to the collimator as a separate housing. The collimator is usually provided at a radiation port of the tubular bulb 33, controls the irradiation area of radiation R. and irradiates the subject S with a field light that indicates the irradiation area of radiation R.

The visible light camera is also capable of generating a visible light image of the positioned subject S by taking an image of the area irradiated with radiation R.

The visible light camera is also capable of communicating with any one or more of the devices 1 to 3 via a communication network N. The communication network N may be a wired communication, a wireless communication, or a combination of wired and wireless communication.

The visible light camera receives instructions for visible light image generation via the communication network N, generates a visible light image based on the instructions, and transmits the generated visible light image to a designated device.

For example, the visible light camera receives instructions from the generator 31 to generate a visible light image and to transmit the acquired image to the console 2. The generator 31 notifies the visible light camera of the timing information on the start of the pre-imaging, generates a visible light image at the relevant timing, and transmits the visible light image to the console 2 immediately after generation.

Instead of the generator 31, the console 2 may give instructions to the visible light camera to generate a visible light image and to transmit the generated image to the console 2.

The communication unit 23 of the console 2 receives the visible light image, and the controller 21 correlates the visible light image with the corresponding pre-image and stores them in the storage 22. This process is executed for each pre-imaging. In this way, the visible light image that shows the positioning state of the subject S at each pre-imaging can be stored in association with the corresponding pre-image.

Furthermore, when the display 24 displays the pre-image, the console 2 causes the visible light image corresponding to the pre-image to be displayed on the display 24.

This allows the radiographer to simultaneously view the positioning state and the pre-image for comparison, and to efficiently identify the cause of positioning errors.

The controller 21 may identify an irradiation field of radiation in the visible light image by an image recognition process, cut out an image of the irradiation portion to generate an irradiation portion visible light image, store it in the storage 22 in correspondence with the pre-image, and use it as a visible light image to be displayed on the display 24 described above.

Furthermore, the controller 21 may identify an irradiation field of radiation R in the pre-image by an image recognition process, cut out an image of the irradiation portion to generate an irradiation portion pre-image, store it in the storage 22 in correspondence with the pre-image, and use it as a pre-image to be displayed on the display 24 described above.

When the display 24 simultaneously displays the irradiation portion visible light image and the irradiation portion pre-image that show the same area, the radiographer can more efficiently identify the cause of positioning errors. When the display 24 simultaneously displays the irradiation portion visible light image and the irradiation portion pre-image in the same size, the efficiency is further improved.

The visible light image and the pre-image may be displayed side by side or overlapped on each other. They are displayed overlapped on each other without displacement by alignment of the area of the irradiation field of the visible light image and the area of the irradiation field of the pre-image, it is possible to prevent misalignment.

When the console 2 executes the positioning judgment process, the judgment result may be displayed on the display 24 together with (for example, superimposed on) these two images.

When the irradiation field of the visible light image is identified by the image recognition process, identification errors are less likely to occur by identifying the irradiation field based on the information on the boundary of the irradiation field light that appears in the visible light image.

However, the irradiation field light is usually turned on and off based on the operations of the operation interface attached to the collimator, the operation interface 25 of the console 2, the illumination field light ON/OFF switching button on the tubular bulb operation interface that is a combination of the tubular bulb display 33a and the touch panel laminated to it, and the like. Therefore, the illumination field light is not always turned on at the start of the pre-imaging.

In order to deal with this situation, the collimator is made to be able to communicate with airy one or more of the devices 1 to 3 via the communication network N. In this way, the generator 31 or console 2 can instruct the collimator to turn on the irradiation field light at the start of the pre-imaging based on the pre-imaging start timing information so that the collimator can turn on the illumination field light according to the instruction. By doing so, the illumination field light is reliably captured in the visible light image, thus reducing errors in identification of the illumination field.

In the above, the method of displaying the pre-image, the corresponding visible light image, and the positioning judgment result on display 24 of console 2 has been explained, but they are not limited to be displayed on the display 24.

For example, if the tubular bulb display 33a displays them, when the user executes positioning again after the completion of pre-imaging, the user can think about the points to be corrected on the spot while referring to the pre-image and visible light image displayed on the tubular bulb display 33a.

Also, when only the pre-image is displayed, the user needs to imagine the positioning from the radiation image (pre-image). However, when both the pre-image and visible light image are displayed, the user does not need to imagine, which increases efficiency and improves the accuracy of positioning adjustment.

The method of displaying a plurality of pre-images on the tubular bulb display 33a has already been explained, and the same is true when the re are visible light images.

That is, in the same way as the pre-image, a plurality of visible light images can be displayed on the tubular bulb display 33a. At this time, the user can easily compare the pre-image and visible light image when the corresponding pre-image and visible light image are displayed as a set (for example arranged next to each other or overlapped with each other).

In the above, the method of using visible light images taken by a visible light camera, but the images used are not limited to the visible light images as long as the user can grasp positioning from the image.

For example, instead of the visible light image, an infrared image taken by an infrared camera can be used Since infrared light has a longer wavelength than visible light and can penetrate clothing, it can be used to capture the subject's skin. Therefore, it is possible to obtain images that are more suitable for positioning than visible light, and positioning accuracy is improved.

Instead of the visible light image, a distance image may be used. The distance image is generated by a distance image camera (TOF camera) and is an image of the distance of an object from the camera. In the distance image, the color of each pixel is determined according to the distance. Therefore, for example, when the subject S changes its orientation, the distance of subject S from the camera changes, and the color changes even in the same image of subject S. Therefore, by using a distance image instead of a visible light image, it becomes easier to grasp the change in the orientation of the subject S, and the positioning orientation becomes easier to grasp.

In the above, the configuration in which an infrared image or a distance image is used instead of a visible light image has been described, but one or more of a visible light image, an infrared image, or a distance image may be combined. By combining them, it is possible to generate multiple pieces of information that can only be obtained from each image, which makes it possible to better understand the positioning and facilitates positioning adjustment.

4. Others

Next, modified Examples of the above imaging control apparatus 2, 31A, 4 or system 100, 100A, 100B will be explained.

Modified Example 1

In either of the control modes, pre-image checking mode and short-time imaging mode, the imaging conditions for the main imaging are derived based on the pre-image. Therefore, when a lot of noise is contained in the pre-image, the accuracy of deriving the imaging conditions for main imaging will be reduced.

Therefore, regardless of which control mode is used from before start of pre-imaging to at least the end of the pre-imaging, the controller 21 may set other devices (not shown in the drawings, and for example, an oscillating grid, an automatic exposure control (AEC) system using a photo timer, and the like) that generate electromagnetic waves, which may cause noise, to a state in which noise generation is suppressed (for example, in a state where the power is turned off, or the power consumption is suppressed).

In this case, the state in which noise generation is suppressed may be kept until the end of the main imaging. In this way, the processes to be executed from the completion of the pre-imaging to the start of the main imaging can be simplified, thereby allowing the time between the completion of the pre-imaging and the start of the main imaging to be shortened.

Modified Example 2

In the above imaging control process, before executing the pre-imaging, the controller 21 may compare the heat unit values of the tubular bulb 33 and the generator 31 with preset limit values, and if the controller 21 determines that the heat unit values exceed the limit values, the controller 21 may not allow subsequent imaging. In this case, the controller 21 may acquire the heat unit values by, for example, calculating the increase in the heat unit value when imaging is executed under the set imaging conditions, or by estimating with reference to a table showing the relationship between the imaging conditions and the increase in the heat unit value.

Even if the heat unit values before the start of pre-imaging do not exceed the limit values and the pre-imaging can be executed, if the heat unit value before the start of main imaging exceeds the limit value, it is necessary to wait for the heat unit values to drop before starting main imaging. Then, the subject S moves relatively largely, and it becomes difficult to combine the pre-imaging and main imaging.

Therefore, in the short-time imaging mode, the controller 21 desirably checks whether or not the heat unit values (the maximum heat unit values) after completing the pre-imaging and main imaging are to exceed the limit values before starting the pre-imaging, and does not allow imaging if they exceed live limit values.

Before the start of the pre-imaging, the irradiation time or the tube current-time product to be used for the main imaging has not yet been determined. Therefore, the heat unit values are calculated using the voltage values used in the pre-imaging and main imaging, the upper limit of the sum of the irradiation time for the pre-imaging and the irradiation time for the main imaging, or the tube voltage values used in the pre-imaging and main imaging and the upper limit of the sum of the product of a tube current and the time for the pre-imaging and the product of a tube current and the time for the main imaging.

In this way, the maximum heat unit values can be determined.

In the pre-imaging checking mode, before pre-imaging is started, the upper limit values of the tube voltage value, tube current value and irradiation time used for main imaging, or the upper limit values of the tube voltage value and the product value of tube current and time are displayed.

When at least one of the tube voltage value, tube current value, irradiation time, and tube current-time product is configured to be changeable, it is desirable to acquire the heat unit values (maximum heat unit values) after completing the pre-imaging and main imaging in the same way as in the aforementioned short-time imaging mode, to check whether or not the values exceed the limit values, and if they do, not to allow the imaging.

Meanwhile, when imaging conditions are not displayed before the pre-imaging, the controller 21 may check the heat unit value alter the pre-imaging before starting the pre-imaging, check the heat unit value after the main imaging before the main imaging, or calculate the heat unit values (maximum heat unit values) after the pre-imaging and main imaging in the same way as in the aforementioned short-time imaging mode using irradiation time used for main imaging or the predetermined upper limit value of the product value of tube current and time to check whether or not the heat unit values after the pre-imaging and main imaging exceed the limit values, and if they do, not to allow the imaging.

Modified Example 3

Figures 13, 14A, 14B:
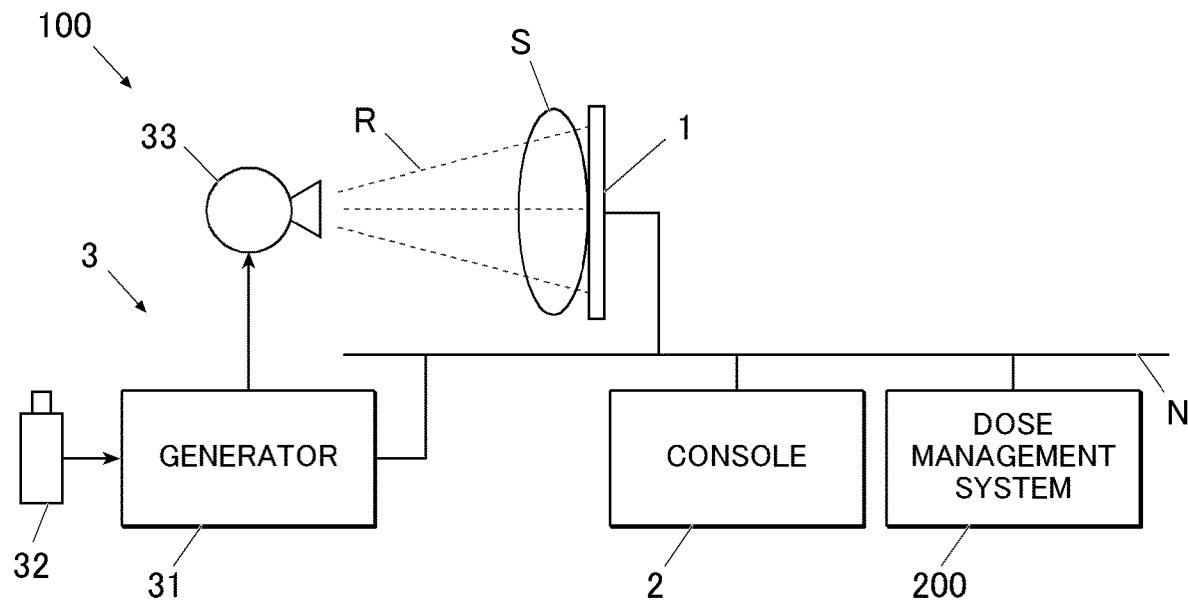
FIG. 13 is a block diagram showing the radiation imaging system and a dose management system of FIG. 1, FIG. 3, and FIG. 4.
FIG. 14A is an example of a table slewing information managed by the dose management system of FIG. 13.
FIG. 14B is an example of a table slewing information managed by the dose management system of FIG. 13.

For example, as shown in FIG. 13, the system 100 may be able to communicate with a dose management system 200 via a communication network N.

Then, each time the system 100 executes imaging, the system 100 may transmit the subject ID, imaging method, imaging results, radiation dose, and the like to the dose management system 200.

Upon receiving various kinds of information from the system 100, the dose management system 200 calculates the cumulative radiation dose, rate of retaking images, and the like for each subject S based on the various information received, and manages the calculated values in the form of a table $T_2$ as shown in FIG. 14A, for example.

The dose management system 200 may manage radiation doses for at least one of respective imaging sites and respective imaging techniques.

In this case, in the imaging control process, the controller 21 may switch the control mode based on the values managed by the dose management system.

Specifically, for example, before executing the acquisition process, the controller 21 retrieves the retaken rate of the subject S to be imaged from the dose management system 200.

Then, when it is determined that the recalled retaken rate is the preset threshold or more, the controller 21 switches the control mode to the pre-image checking mode, and when it is determined that it is less than the threshold, the controller 21 switches it to the short-time imaging mode.

For example, when a side view of a knee joint of subject S whose ID is A is to be taken from now, according to the table T2 shown in FIG. 14A, the retaken rate retrieved from the dose management system 200 is 20%, and thus the controller 21 switches the control mode to the pre-image checking mode.

When configured as described above, the controller 21 may select a control mode not based on the retaken rate throughout the lifetime, but based on the retaken rate in a recent predetermined period (for example, one year). The retaken rate vanes depending on the age, past surgical history, and the like of the subject S. Therefore, the above configuration makes it possible to select a control mode that is more suitable for the actual condition of the subject S.

Upon receiving various kinds of information from the system 100, the dose management system 200 may calculate the re-taking rate and the like for each user based on the received various kinds of information, and manage the calculated values in the form of a table $T_3$ as shown in FIG. 14B, for example.

Then, the controller 21 may switch the control mode not based on the retaking rate of the subject S, but based on the retaking rate of the user.

Specifically, if it is determined that the retaking rate of the user is a preset threshold or more, the controller 21 switches the control mode to the pre-image checking mode, and if it is determined that the retaking rate is less than the preset threshold, the controller 21 switches the control mode to the short-time imaging mode.

When the retaking rate of the user is used, the control mode may also be selected based on the retaking rate for a predetermined period of time (for example, one year). The retaking rate of the user varies depending on the user's experience period and the like. Therefore, the above configuration makes it possible to select a control mode that is more suitable for the actual condition of the user.

5. EFFECTS

The imaging control apparatus 2, 31A, 4 or the system 100, 100A, 100B described above T switches the control mode of the controller 21 to the pre-image checking mode in which the pre-image is displayed after executing the pre-imaging, or to the short-time imaging mode in which the main imaging is executed without displaying the pre-image alter executing the pre-imaging, and notifies in which control mode the controller 21 is in, the pre-image checking mode or the short-time imaging mode.

Therefore, according to the imaging control apparatus 2, 31A, 4 or the system 100, 100A, 100B, when executing two-step radiation imaging including pre-imaging and main imaging, it is possible to use a single device for both of the two kinds of imaging with different possibilities of failure due to different imaging attributes and to make it sure that the user knows whether or not the pre-image is to be displayed after the pre-imaging.

6. Others

Although embodiments of the present invention have been described and illustrated in detail, the disclosed embodiments are made for purposes of illustration and example only and not limitation. The scope of the present invention should be interpreted by terms of the appended claims.

In the above example, a hard disc drive or non-volatile semiconductor memory is used as a computer-readable medium for the program according to the present invention, but the medium is not limited thereto. A portable storage medium such as CD-ROM can also be used as the computer-readable storage medium. A carrier wave can also be applied to the present invention as a medium for that provides data of a program according to the present invention.

What is claimed is:

1. A radiation imaging system comprising a first hardware processor that executes control such that, before main imaging is executed at a main dose, pre-imaging is executed at a pre-dose that is lower than the main dose,
the first hardware processor being configured to execute the control in a pre-image checking mode and a short time imaging mode,
the first hardware processor deriving an imaging condition for the main imaging based on a pre-image acquired in the pre-imaging, switching a control mode to one of the pre-image checking mode and the short-time imaging mode before pre-imaging is executed, and notifying which control mode between the pre-image checking mode and the short-time imaging mode is used to execute the control, wherein the first hardware processor switches the control mode based on imaging attribute information including at least one of imaging technique information, subject attribute information, radiographer information, imaging purpose and place information, and usage device information,
upon the first hardware processor executing the control in the pre-image checking mode, the first hardware processor displays the pre-image after executing the pre-imaging, waits for operation of an irradiating instruction switch after executing the pre-imaging, and executes the main imaging after the irradiating instruction switch is operated, and
upon the first hardware processor executing the control in the short-time imaging mode, the first hardware processor does not display the pre-image after executing the pre-imaging and automatically executes the main imaging.

2. The radiation imaging system according to claim 1, wherein the first hardware processor is configured to execute judgment on whether or not the positioning is appropriate,
wherein, upon the first hardware processor executing the control in the pre-image checking mode, the first hardware processor executes the judgment, and
wherein, upon the first hardware processor executing the control in the short-time imaging mode, the first hardware processor does not execute the judgment.

3. The radiation imaging system according to claim 2, wherein the first hardware processor analyzes the pre-image, and
wherein, upon the first hardware processor executing the control in the pre-image checking mode, the first hardware processor executes the judgment based on a result of analyzing the pre-image.

4. The radiation imaging system according to claim 1, wherein the first hardware processor further switches the control mode after the pre-imaging based on at least one of results of the pre-imaging, the results including determination of abnormality in density based on the pre-image, artifact detection based on the pre-image, determination of subject type based on the pre-image, communication abnormality detection or communication delay detection in the pre-imaging, abnormality determination in an actual value of imaging condition or irradiated pre-dose in the pre-imaging, and detection of abnormal operation or device abnormality in the pre-imaging.

5. The radiation imaging system according to claim 1, wherein the first hardware processor is configured to execute combination of the pre-image and a main image that is acquired in the main imaging to generate a combination image, and
wherein, upon each switching of the control mode, the first hardware processor sets whether or not to execute the combination.

6. The radiation imaging system according to claim 1, further comprising:
a situation transmitter selected from the group consisting of a display, a monitor, an irradiating instruction switch, a speaker, and a lamp,
wherein the first hardware processor and the situation transmitter transmit a situation of operation,
upon the first hardware processor executing the control in the short-time imaging mode, a content transmitted by the first hardware processor and the situation transmitter during a period from completion of the pre-imaging to start of the main imaging is the same as a content transmitted during the pre-imaging and the main imaging, and wherein, upon the first hardware processor executing the control in the pre-image checking mode, a content transmitted by the first hardware processor and the situation transmitter during a period from completion of the pre-imaging to start of the main imaging is different from a content transmitted during the pre-imaging and the main imaging.

7. The radiation imaging system according to claim 1, further comprising:

a display that displays a tube voltage, a tube current, and irradiation time, or a tube voltage and a product of tube current and time, wherein, upon the first hardware processor executing the control in the short-time imaging mode, the first hardware processor and the display display, before the pre-imaging is executed, either of:

a tube voltage value and a tube current value for the pre-imaging, a tube voltage value and a tube current value for the main imaging, and an upper limit of a sum of an irradiation time for the pre-imaging and an irradiation time for the main imaging; and a tube voltage value for the pre-imaging, a tube voltage value for the main imaging, and an upper limit of a sum of a product of a tube current and a time for the pre-imaging and a product of a current and a time for the main imaging, and wherein, upon the first hardware processor executing the control in the pre-image checking mode, the first hardware processor and the display display, before the pre-imaging is executed, either of:

a tube voltage value, a tube current value, and an irradiation time for the pre-imaging; and a tube voltage value and a product of a tube current and a time for the pre-imaging, and further display, before the main imaging is executed, either of:

a tube voltage value, a tube current value, and an irradiation time for the main imaging; and a tube voltage value and a product of a tube current and a time for the main imaging.

8. The radiation imaging system according to claim 7, further comprising:

an operation interface that is configured to be operated by a user, wherein, upon the first hardware processor executing the control in the pre-image checking mode, the first hardware processor is configured to be capable of changing, during a period from completion of the pre-imaging to start of the main imaging based on an operation executed on the operation interface, either of:

a tube voltage value, a tube current value, and an irradiation time for the main imaging; and a tube voltage value and a product of a tube current and a time for the main imaging.

9. The radiation imaging system according to claim 1, wherein, upon the first hardware processor executing the control in the short-time imaging mode, the first hardware processor derives the imaging condition such that pixels of a radiation image that is finally generated with radiation of a total dose of the pre-dose and the main dose have desired density, and wherein, upon the first hardware processor executing the control in the pre-image checking mode, the first hardware processor derives the imaging condition such that pixels of a radiation image that is finally generated only with radiation of the main dose have desired density.

10. The radiation imaging system according to claim 9, wherein the first hardware processor is configured to execute combination of the pre-image and a main image that is acquired in the main imaging to generate a combination image, wherein, upon each switching of the control mode, the first hardware processor sets whether or not to execute the combination, and wherein, upon the first hardware processor selecting to execute the combination, even upon the first hardware processor executing the control in the short-time imaging mode, the first hardware processor derives the imaging condition such that pixels of a radiation image that is finally generated only with radiation of main dose have desired density.

11. The radiation imaging system according to claim 1, further comprising:

a second hardware processor that controls a state of a tubular bulb that generates radiation, wherein, upon the first hardware processor executing the control in the pre-image checking mode, the second hardware processor temporarily cancels an irradiation-ready state of the tubular bulb in a period from completion of the pre-imaging to start of the main imaging, and wherein, upon the first hardware processor executing the control in the short-time imaging mode, the second hardware processor continues to be in an irradiation-ready state of the tubular bulb in a period from completion of the pre-imaging to start of the main imaging.

12. The radiation imaging system according to claim 11, wherein the first hardware processor determines whether or not the imaging condition satisfies a predetermined condition, wherein, upon the first hardware processor determining that the imaging condition satisfies the predetermined condition, even upon the first hardware processor executing the control in the pre-image checking mode, the second hardware processor continues to be in the irradiation-ready state of the tubular bulb.

13. The radiation imaging system according to claim 1, wherein the first hardware processor executes the control such that radiation emission and image generation are repeated several times in executing the main imaging once.

14. An imaging control apparatus that is a part of a radiation imaging system comprising a first hardware processor that executes control such that, before main imaging is executed at a main dose, pre-imaging is executed at a pre-dose that is lower than the main dose, the first hardware processor being configured to execute the control in a pre-image checking mode and a short time imaging mode, the first hardware processor deriving an imaging condition for the main imaging based on a pre-image acquired in the pre-imaging, switching a control mode to one of the pre-image checking mode and the short-time imaging mode before pre-imaging is executed, and outputting which control mode between the pre-image checking mode and the short-time imaging mode is used to execute the control, wherein the first hardware processor switches the control mode based on imaging attribute information including at least one of imaging technique information, subject attribute information, radiographer information, imaging purpose and place information, and usage device information, upon the first hardware processor executing the control in the pre-image checking mode, the first hardware processor displays the pre-image after executing the pre-imaging, waits for operation of an irradiating instruction switch after executing the pre-imaging, and executes the main imaging after the irradiating instruction switch is operated, and upon the first hardware processor executing the control in the short-time imaging mode, the first hardware processor does not display the pre-image after executing the pre-imaging and automatically executes the main imaging.

15. A radiation imaging method using a radiation imaging system comprising a first hardware processor that executes control such that, before main imaging is executed at a main dose, pre-imaging is executed at a pre-dose that is lower than the main dose and deriving an imaging condition for the main imaging based on a pre-image acquired in the pre-imaging, the first hardware processor being configured to execute the control in a pre-image checking mode and a short time imaging mode, the method comprising:

switching a control mode of the first hardware processor to one of the pre-image checking mode and the short-time imaging mode before pre-imaging is executed, wherein the control mode of the first hardware processor is switched based on imaging attribute information including at least one of imaging technique information, subject attribute information, radiographer information, imaging purpose and place information, and usage device information;

notifying the radiation imaging system which control mode between the pre-image checking mode and the short-time imaging mode the first hardware processor is using to execute the control;

when switched to the pre-image checking mode, after executing the pre-imaging, the first processor displays the pre-image, waits for operation of an irradiating instruction switch, and executes the main imaging after the irradiating instruction switch is operated, and when switched to the short-time imaging mode, the first processor does not display the pre-image after executing the pre-imaging and automatically executes the main imaging.

* * * * *